(12) United States Patent
Nishida et al.

(10) Patent No.: US 8,366,956 B2
(45) Date of Patent: *Feb. 5, 2013

(54) QUATERNARY AMMONIUM SALT AND COMPOSITION, AND ELECTROCHEMICAL DEVICE

(75) Inventors: Tetsuo Nishida, Izumiotsu (JP);
Yasutaka Tashiro, Izumiotsu (JP);
Megumi Tomisaki, Izumiotsu (JP);
Masashi Yamamoto, Izumiotsu (JP);
Kazutaka Hirano, Izumiotsu (JP);
Akihiro Nabeshima, Tokushima (JP);
Hiroaki Tokuda, Tokushima (JP); Kenji Sato, Saitama (JP); Takashi Higono, Utsunomiya (JP)

(73) Assignees: Otsuka Chemical Co., Ltd., Osaka (JP); Stella Chemifa Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/926,313

(22) Filed: Nov. 9, 2010

(65) Prior Publication Data

US 2011/0123873 A1      May 26, 2011

Related U.S. Application Data

(62) Division of application No. 10/563,125, filed as application No. PCT/JP2004/009623 on Jun. 30, 2004, now Pat. No. 7,834,197.

(30) Foreign Application Priority Data

Jul. 1, 2003   (JP) .................. 2003-270225

(51) Int. Cl.
*C07D 207/06*   (2006.01)
*H01L 31/04*   (2006.01)

(52) U.S. Cl. ..................... 252/62.2; 548/570

(58) Field of Classification Search .................. 548/570
See application file for complete search history.

(56) References Cited

U.S. PATENT DOCUMENTS

| 2003/0202316 A1 | 10/2003 | Kawasato et al. | 361/502 |
| 2004/0094741 A1 | 5/2004 | Sato et al. | 252/1 |
| 2006/0034035 A1 | 2/2006 | Maruo et al. | 361/502 |
| 2006/0035137 A1 | 2/2006 | Maruo et al. | 429/46 |

FOREIGN PATENT DOCUMENTS

WO    02/076924    10/2002

OTHER PUBLICATIONS

Pernak, J. et al., "Antistatische Eigenschaften von Pyrrolidinium-, Morpholinium-und Pyridinium-Chloriden mit Alkoxymethyl- und Alkylthiomethylrest", *Tenside Surf. Det.*, 30 (1993) pp. 328-330.
Matsumoto, H. et al., "Improvement of Ionic Conductivity of Room Temperature Molten Salt Based on Quaternary Ammonium Cation and Imide Anion," *Electrochemical Society Proceedings*, vol. 99-41, 2000, pp. 186-192.
Xu, Kang et al., "Quaternary Onium Salts as Nonaqueous Electrolytes for Electrochemical Capacitors," *Journal of the Electrochemical Society*, 148 (3), A267-A274, 2001.
RN 151263-00-2, retrueved from CAPLUS on Nov. 3, 2009.

*Primary Examiner* — Shawquia Young
(74) *Attorney, Agent, or Firm* — Kubovcik & Kubovcik

(57) ABSTRACT

A quaternary ammonium salt of the formula (1), a composition containing the quaternary ammonium salt and an organic solvent, and an electrochemical device using the salt (1)

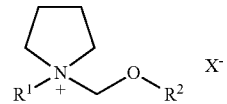

wherein $R^1$ and $R^2$ are both methyl and $X^-$ is $BF_4^-$ or $N(CF_3SO_2)_2^-$.

12 Claims, 5 Drawing Sheets

QUATERNARY AMMONIUM SALT AND COMPOSITION, AND ELECTROCHEMICAL DEVICE

This application is a division of application Ser. No. 10/563,125, filed Jun. 26, 2006, now U.S. Pat. No. 7,834,197 which is a 371 of international application PCT/JP2004/009623, filed Jun. 30, 2004, which claims priority based on Japanese Patent Application No. 2003-270225, filed Jul. 1, 2003, and which are incorporated herein by reference.

TECHNICAL FIELD

The present invention relates to quaternary ammonium salts, electrolytes, electrolytic solutions and electrochemical devices. More particularly, the invention relates to functional materials which are usable as electrolytes having a high solubility in organic solvents, high voltage resistance and high electrical conductivity.

BACKGROUND ART

In recent years, higher output densities and improved energy densities have been required of electrochemical devices including cells and capacitors. Organic electrolytic solutions have found wider use than aqueous electrolytic solutions from the viewpoint of voltage resistance. Examples of organic electrolytic solutions are those prepared by dissolving alkali metal salts or solid ammonium salts in an organic solvent such as propylene carbonate. Electrolytic solutions of the former type are used for lithium ion cells, while those of the latter type are used for electric double-layer capacitors. Organic electrolytic solutions are inferior to aqueous solutions in electrical conductivity, and numerous studies have been made on organic solvents or electrolytes to obtain improved electrical conductivity. As a result, Patent literature 1 (JP 1991-58526 A) discloses asymmetric ammonium salts for use as electrolytes for electric double-layer capacitors. Ue et al., J. Electrochem. Soc. 141(2989) 1994 shows detailed investigations into kinds of tetraalkylammonium salts and electrical conductivity thereof. Tetraethylammonium tetrafluoroborate and triethylmethylammonium tetrafluoroborate are generally in use.

The electrical conductivity of nonaqueous electrolytic solutions comprising such a solid electrolyte dissolved in a solvent varies with the concentration of the electrolyte. With a rise in the concentration, the ion concentration of the solution increases to increase the electrical conductivity, which will reach a maximum in due course. The electrical conductivity reaching the maximum starts to decrease presumably because the electrolyte becomes difficult to dissociate and increases in viscosity at the same time owing to increased interaction between the solvent and ions and between the ions as the number of ions increases in the electrolytic solution. When further increasing in concentration, the electrolyte becomes no longer dissociable, and the concentration of the electrolyte levels off. Thus, an attempt to increase the concentration of the electrolyte encounters the problem that the electrolyte becomes less soluble. Another problem is also experienced in that when electrolytic solutions having an electrolyte dissolved therein at a high concentration is used in an environment of low temperature, a salt will separate out to impair the electrical conductivity of the solution. Solvents of high dielectric constant are usually preferred for dissociating electrolytes to a higher degree, and propylene carbonate, ethylene carbonate, gamma-butyrolactone, etc. are in use. Suitable to use as electrolytes are tetraethylammonium tetrafluoroborate, triethylmethylammonium tetrafluoroborate and the like which are relatively soluble in solvents of high dielectric constant, whereas these electrolytes are limited in solubility to a concentration of about 2 M at room temperature and have the disadvantage of permitting separation of crystals when to be dissolved to higher concentrations or at lower temperatures. These electrolytes are almost insoluble in solvents of low dielectric constant, failing to form electrolytic solutions which are useful as such.

When propylene carbonate, ethylene carbonate, gamma-butyrolactone or the like is used as the solvent for applications necessitating a high voltage, the electrolyte is governed by the solvent decomposition voltage even if the electrolyte has high voltage resistance, with the result that the conventional capacitors are limited to about 2.5 V in operating voltage if highest. If the capacitor is operated at voltage exceeding 2.5 V, the electrolytic solution (mainly the solvent) undergoes electrochemical decomposition, becomes seriously impaired in performance and produces undesirable phenomena such as evolution of gas. In the application of capacitors as energy storage devices to mobile bodies such as hybrid cars and electric motor vehicles, improved energy capacities are demanded, and a higher operating voltage is effective means for giving an improved energy density, whereas it has been impossible to improve the voltage resistance with use of conventional electrolytic solutions, hence a need for electrolytes and solvents of higher voltage resistance. Although chain carbonate solvents are solvents of higher voltage resistance, conventional electrolytes such as tetraethylammonium tetrafluoroborate and triethylmethylammonium tetrafluoroborate are low in solubility in these solvents which are low in dielectric constant, and are not usable as electrolytic solutions.

Found in recent years are salts having a melting point around room temperature or salts having a melting point not higher than room temperature (salts melting at room temperature). It is known that even if solid at room temperature, such salts dissolve in organic solvents at a higher concentration than usual electrolytes. Furthermore, the salts melting at room temperature are miscible with a specific organic solvent in a desired ratio. Accordingly, these salts afford electrolytic solutions having a high concentration not available by dissolving conventional solid electrolytes in organic solvents, while although having a high concentration, the solution is less likely to encounter the problem that the salt will separate out in a low-temperature environment. The salt melting at room temperature is itself liquid and is therefore usable singly as an electrolyte.

It is also known that salts melting at room temperature, although liquid, are low in vapor pressure and not easily combustible because they comprise ions only. Accordingly, when dissolved in an organic solvent at a high concentration, the salt melting at room temperature serves as a flame retardant for electrolytic solutions.

Typical of such salts melting at room temperature is 1-ethyl-3-methylimidazolium tetrafluoroborate ($EMI.BF_4$). The salt $EMI.BF_4$ has a high electrical conductivity, and the application of this salt to electrochemical devices including lithium secondary cells and electric double-layer capacitors is under study. However, the imidazolium salt is about 4 V in electrochemical stability, such that when applied to electric double-layer capacitors, the salt is about 2.5 V in the upper limit of operating voltage and is still in limited use.

Research has been made in recent years on salts melting at room temperature and stable in a wider potential range. For example, salts melting at room temperature and comprising a cationic component with an aliphatic ammonium skeleton as disclosed in Patent Literature 2 (Japanese Patent No. 2981545) are at least 5.8 V in voltage resistance and are considered to be applicable to lithium secondary cells. The salts melting at room temperature and having an aliphatic ammonium skeleton in the cationic component nevertheless have the drawback of being generally high in viscosity and low in electrical conductivity. Although improved in electrical conductivity when mixed with an organic solvent, the conductivity level is still lower than that of the solutions of conventional solid electrolytes in organic solvents.

Patent Literature 3 (WO 02/076924) discloses that aliphatic ammonium salts having an alkoxyalkyl group introduced thereinto are highly soluble in a nonaqueous organic solvent and are less likely to separate out at low temperatures, while electrolytes still higher in solubility in organic solvents, voltage resistance and electrical conductivity are demanded.

Even in the case where the salts melting at room temperature, having diethylmethylmethoxyethylammonium as a cation component and disclosed in Patent Literature 3 are dissolved in an organic solvent, the solutions are lower in electrical conductivity than the electrolytic solutions prepared by dissolving conventional solid electrolytes (e.g., triethylmethylammonium tetrafluoroborate, etc.) in an organic solvent. The disclosed salts still remain to be improved in solubility in a chain carbonate, and electrolytes are demanded which are higher in solubility in organic solvents, voltage resistance and electrical conductivity.

An object of the present invention is to provide a quaternary ammonium salt which is high in electrical conductivity and voltage resistance.

Another object of the invention is to provide an electrolyte which is high in solubility in organic solvents, voltage resistance and electrical conductivity.

Another object of the invention is to provide an electrolytic solution which is high in voltage resistance and electrical conductivity.

Another object of the invention is to provide an electrolyte which affords an electrolytic solution of high electrolyte concentration when dissolved in a solvent and consequently provide an electrochemical device usable at a high voltage and having a high discharge capacity and great current discharge performance.

DISCLOSURE OF THE INVENTION

The present invention provides a quaternary ammonium salt of the formula (1)

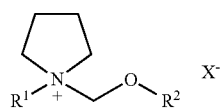

(1)

wherein $R^1$ is straight-chain or branched alkyl having 1 to 4 carbon atoms, $R^2$ is methyl or ethyl, and $X^-$ is a fluorine-containing anion, the salt being an electrolyte.

The invention also provides a quaternary ammonium salt of the formula (2)

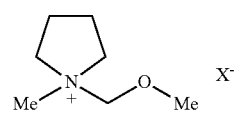

(2)

wherein $X^-$ is a fluorine-containing anion, and Me is methyl, the salt being an electrolyte.

We have conducted intensive research to develop novel chemical substances which fulfill the object of exhibiting improved electrical conductivity, and consequently found that cations having an N,O-acetal skeleton structure of the formula (1) in the molecule have high electrical conductivity, and that an ammonium cation included among these cations and having a pyrrolidine skeleton and an N,O-acetal group is especially high in electrical conductivity, voltage resistance and solubility in organic solvents.

The mode of practicing the present invention will be described below.

The present invention provides quaternary ammonium salts of the formula (1) which are composed of a quaternary ammonium cation and a fluorine-containing anion. Examples of quaternary ammonium cations are N-methyl-N-methoxymethylpyrrolidinium cation (N-methoxymethyl-N-methylpyrrolidinium cation), N-ethyl-N-methoxymethylpyrrolidinium cation, N-methoxymethyl-N-n-propylpyrrolidinium cation, N-methoxymethyl-N-iso-propylpyrrolidinium cation, N-n-butyl-N-methoxymethylpyrrolidinium cation, N-iso-butyl-N-methoxymethylpyrrolidinium cation, N-tert-butyl-N-methoxymethylpyrrolidinium cation, N-ethoxymethyl-N-methylpyrrolidinium cation, N-ethyl-N-ethoxymethylpyrrolidinium cation (N-ethoxymethyl-N-ethylpyrrolidinium cation), N-ethoxymethyl-N-n-propylpyrrolidinium cation, N-ethoxymethyl-N-iso-propylpyrrolidinium cation, N-n-butyl-N-ethoxymethylpyrrolidinium cation, N-iso-butyl-N-ethoxymethylpyrrolidinium cation and N-tert-butyl-N-ethoxymethylpyrrolidinium cation.

More preferable are N-methyl-N-methoxymethylpyrrolidinium cation (N-methoxymethyl-N-methylpyrrolidinium cation), N-ethyl-N-methoxymethylpyrrolidinium cation and N-ethoxymethyl-N-methylpyrrolidinium cation. Examples of fluorine-containing anions are $CF_3CO_2^-$, $CF_3SO_3^-$, $N(CF_3SO_2)_2^-$, $N(CF_3CF_2SO_2)_2^-$, $C(CF_3SO_2)_3^-$, $N(CF_3SO_2)(CF_3CO)^-$, $BF_4^-$ and $PF_6^-$. $F^-$ is not included. Preferable are $CF_3SO_3^-$, $N(CF_3SO_2)_2^-$, $N(CF_3CF_2SO_2)_2^-$ and $C(CF_3SO_2)_3^-$. More preferable are $CF_3CO_2^-$, $N(CF_3SO_2)_2^-$, $BF_4^-$ and $PF_6^-$. Particularly preferable are $N(CF_3SO_2)_2^-$ and $BF_4^-$. Especially preferable salts which are combination of these cations and anions are N-methyl-N-methoxymethylpyrrolidinium tetrafluoroborate (N-methoxymethyl-N-methylpyrrolidinium tetrafluoroborate), N-ethyl-N-methoxymethylpyrrolidinium tetrafluoroborate, N-ethoxymethyl-N-methylpyrrolidinium tetrafluoroborate, N-methyl-N-methoxymethylpyrrolidinium bistrifluoromethanesulfonylimide (N-methoxymethyl-N-methylpyrrolidinium bistrifluoromethanesulfonylimide), N-ethyl-N-methoxymethylpyrrolidinium bistrifluoromethanesulfonylimide, N-ethoxymethyl-N-methylpyrrolidinium bistrifluoromethanesulfonylimide, N-methyl-N-methoxymethylpyrrolidinium trifluoromethanesulfolate (N-methoxymethyl-N-methyltrifluoromethanesulfolate).

The quaternary ammonium salts provided by the present invention are salts melting at room temperature and the salts per se are usable as liquid electrolytes. In this case, one of the salts is usable singly, or at least two kinds of salts may be used in admixture.

When to be used as an electrolyte, the quaternary ammonium salt obtained by the invention may be used as admixed with a suitable organic solvent. Useful solvents include cyclic carbonic acid esters, chain carbonic acid esters, phosphoric acid esters, cyclic ethers, chain ethers, lactone compounds, chain esters, nitrile compounds, amide compounds and sulfone compounds. Examples of such compounds are given below although the solvents to be used are not limited to these compounds.

Examples of cyclic carbonic acid esters are ethylene carbonate, propylene carbonate, butylene carbonate and the like, among which propylene carbonate is preferable.

Examples of chain carbonic acid esters are dimethyl carbonate, ethylmethyl carbonate, diethyl carbonate and the like, among which dimethyl carbonate and ethylmethyl carbonate are preferred.

Examples of phosphoric acid esters are trimethyl phosphate, triethyl phosphate, ethyldimethyl phosphate, diethylmethyl phosphate and the like.

Examples of cyclic ethers are tetrahydrofuran, 2-methyltetrahydrofuran and the like.

Examples of chain ethers are dimethoxyethane and the like.

Examples of lactone compounds are γ-butyrolactone and the like.

Examples of chain esters are methyl propionate, methyl acetate, ethyl acetate, methyl formate and the like.

Examples of nitrile compounds are acetonitrile and the like.

Examples of amide compounds are dimethylformamide and the like.

Examples of sulfone compounds are sulfolane, methyl sulfolane and the like.

Preferable are cyclic carbonic acid esters, chain carbonic acid esters, nitrile compounds and sulfone compounds.

These solvents may be used singly, or at least two kinds of solvents may be used in admixture. Examples of preferred organic solvent mixtures are mixtures of cyclic carbonic acid ester and chain carbonic acid ester such as those of ethylene carbonate and dimethyl carbonate, ethylene carbonate and ethylmethyl carbonate, ethylene carbonate and diethyl carbonate, propylene carbonate and dimethyl carbonate, propylene carbonate and ethylmethyl carbonate and propylene carbonate and diethyl carbonate, mixtures of chain carbonic acid esters such as dimethyl carbonate and ethylmethyl carbonate, and mixtures of sulfolane compounds such as sulfolane and methylsulfolane. More preferable are mixtures of ethylene carbonate and ethylmethyl carbonate, propylene carbonate and ethylmethyl carbonate, and dimethyl carbonate and ethylmethyl carbonate.

When the quaternary ammonium salt of the invention is to be used as an electrolyte, the electrolyte concentration is preferably at least 0.1 M, more preferably at least 0.5 M and most preferably at least 1 M. If the concentration is less than 0.1 M, low electrical conductivity will result, producing electrochemical devices of impaired performance. The upper limit concentration is a separation concentration when the electrolyte is a liquid salt at room temperature. When the solution does not separate, the limit concentration is 100%. When the salt is solid at room temperature, the limit concentration is the concentration at which the solution is saturated with the salt.

The electrolyte of the present invention can be used as admixed with electrolytes other than those of the invention. Examples of electrolytes to be used as admixed with the electrolyte of the invention are alkali metal salts, quaternary ammonium salts, quaternary phosphonium salts, etc. These electrolytes may be used singly, or at least two kinds of them are usable in combination, as admixed with the electrolyte of the invention. Useful alkali metal salts include lithium salts, sodium salts and potassium salts. Examples of such lithium salts are lithium hexafluorophosphate, lithium borofluoride, lithium perchlorate, lithium trifluoromethanesulfonate, sulfonylimide lithium, sulfonylmethide lithium and the like, which nevertheless are not limitative. Examples of useful sodium salts are sodium hexafluorophosphate, sodium borofluoride, sodium perchlorate, sodium trifluoromethanesulfonate, sulfonylimide sodium, sulfonylmethide sodium and the like. Examples of useful potassium salts are potassium hexafluorophosphate, potassium borofluoride, potassium perchlorate, potassium trifluoromethanesulfonate, sulfonylimide potassium, sulfonylmethide potassium and the like although these are not limitative.

Useful quaternary ammonium salts include tetraalkylammonium salts, imidazolium salts, pyrazolium salts, pyridinium salts, triazolium salts, pyridazinium salts, etc., which are not limitative. Examples of useful tetraalkylammonium salts are tetraethylammonium tetrafluoroborate, tetramethylammonium tetrafluoroborate, tetrapropylammonium tetrafluoroborate, tetrabutylammonium tetrafluoroborate, triethylmethylammonium tetrafluoroborate, trimethylethylammonium tetrafluoroborate, dimethyldiethylammonium tetrafluoroborate, trimethylpropylammonium tetrafluoroborate, trimethylbutylammonium tetrafluoroborate, dimethylethylpropylammonium tetrafluoroborate, methylethylpropylbutylammonium tetrafluoroborate, N,N-dimethylpyrrolidinium tetrafluoroborate, N-ethyl-N-methylpyrrolidinium tetrafluoroborate, N-methyl-N-propylpyrrolidinium tetrafluoroborate, N-ethyl-N-propylpyrrolidinium tetrafluoroborate, N,N-dimethylpiperidinium tetrafluoroborate, N-methyl-N-ethylpiperidinium tetrafluoroborate, N-methyl-N-propylpiperidinium tetrafluoroborate, N-ethyl-N-propylpiperidinium tetrafluoroborate, N,N-dimethylmorpholinium tetrafluoroborate, N-methyl-N-ethylmorpholinium tetrafluoroborate, N-methyl-N-propylmorpholinium tetrafluoroborate, N-ethyl-N-propylmorpholinium tetrafluoroborate and the like, whereas these examples are not limitative.

Examples of imidazolium salts are 1,3-dimethylimidazolium tetrafluoroborate, 1-ethyl-3-methylimidazolium tetrafluoroborate, 1,3-diethylimidazolium tetrafluoroborate, 1,2-dimethyl-3-ethylimidazolium tetrafluoroborate and 1,2-dimethyl-3-propylimidazolium tetrafluoroborate, but are not limited to these. Examples of pyrazolium salts are 1,2-dimethylpyrazolium tetrafluoroborate, 1-methyl-2-ethylpyrazolium tetrafluoroborate, 1-propyl-2-methylpyrazolium tetrafluoroborate and 1-methyl-2-butylpyrazolium tetrafluoroborate, but are not limited to these. Examples of pyridinium salts are N-methylpyridinium tetrafluoroborate, N-ethylpyridinium tetrafluoroborate, N-propylpyridinium tetrafluoroborate and N-butylpyridinium tetrafluoroborate, but are not limited to these.

Examples of triazolium salts are 1-methyltriazolium tetrafluoroborate, 1-ethyltriazolium tetrafluoroborate, 1-propyltriazolium tetrafluoroborate and 1-butyltriazolium tetrafluoroborate, but are not limited to these.

Examples of pyridazinium salts are 1-methylpyridazinium tetrafluoroborate, 1-ethylpyridazinium tetrafluoroborate, 1-propylpyridazinium tetrafluoroborate and 1-butylpyridazinium tetrafluoroborate, but are not limited to these.

Examples of quaternary phosphonium salts are tetraethylphosphonium tetrafluoroborate, tetramethylphosphonium tetrafluoroborate, tetrapropylphosphonium tetrafluoroborate, tetrabutylphosphonium tetrafluoroborate, triethylmethylphosphonium tetrafluoroborate, trimethylethylphosphonium tetrafluoroborate, dimethyldiethylphosphonium tetrafluoroborate, trimethylpropylphosphonium tetrafluoroborate, trimethylbutylphosphonium tetrafluoroborate, dimethylethylpropylphosphonium tetrafluoroborate, methylethylpropylbutylphosphonium tetrafluoroborate, but are not limited to these. These are usable singly or in at least two of them.

Useful examples include those given above in which the tetrafluoroborate is replaced by bistrifluoromethanesulfonylimide, hexafluorophosphate or trifluoroacetate.

When the electrolyte of the invention is to be admixed with the above-mentioned electrolyte for use as an electrolyte, the upper limit concentration of the above-mentioned electrolyte to be used in the mixture is a concentration permitting precipitation or separation of the electrolyte. The lower limit concentration of the electrolyte to be used in the mixture depends on the kind of electrochemical device to be fabricated. For example when the electrolyte to be used in the mixture for use as an electrolyte for electric double-layer capacitors, the lower limit concentration thereof is 0 M since the quaternary ammonium salt of the invention alone is usable. For use in lithium cells, at least the above-mentioned lithium salt is used in the mixture. The concentration of the lithium salt is preferably at least 0.1 M to not higher than 2.0 M, more preferably at least 0.15 M to not higher than 1.5 M, further more preferably at least 0.2 M to not higher than 1.2 M. Especially, the preferred concentration is at least 0.3 M to not higher than 1.0 M.

The quaternary ammonium salt (1) of the present invention can be prepared by various processes. Typical of these processes are represented by Equation-1 and Equation-2 given below.

Preparation Process of Equation-1

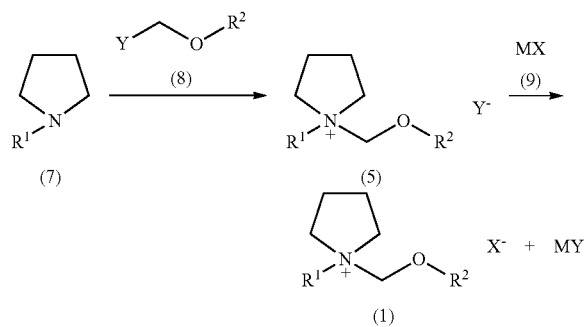

An alkylpyrrolidine of the formula (7) wherein $R^1$ is the same as above is reacted with a compound of the formula (8) wherein $R^2$ is the same as above, and Y is Cl, Br, I or the like to prepare a quaternary ammonium salt of the formula (5), which is then reacted with a compound of the formula (9) to prepare a quaternary ammonium salt of the formula (1) wherein X is other than Y. Represented by M in the formula (9) is one of atoms including hydrogen, alkali metal atoms such as Na, K and Li, alkaline-earth metal atoms such as Ca, Mg and Ba, and metal atoms such as Ag. X is $CF_3CO_2$, $CF_3SO_3$, $N(CF_3SO_2)_2$, $N(CF_3CF_2SO_2)_2$, $C(CF_3SO_2)_3$, $N(CF_3SO_2)(CF_3CO)$, $BF_4$, $PF_6$, etc.

The alkylpyrrolidine of the formula (7) is reacted with the compound of the formula (8), whereby a quaternary ammonium salt of the formula (5) of the invention is prepared.

The alkylpyrrolidine of the formula (7) serving as the starting material and the compound of the formula (8) are both known substances. Examples of alkylpyrrolidines of the formula (7) are methylpyrrolidine, ethylpyrrolidine, n-propylpyrrolidine, isopropylpyrrolidine, n-butylpyrrolidine, isobutylpyrrolidine, tert-butylpyrrolidine, etc. Examples of compounds of the formula (8) are chloromethyl methyl ether, bromomethyl methyl ether, iodomethyl methyl ether, chloromethyl ethyl ether, bromomethyl ethyl ether, iodomethyl ethyl ether, etc. The two compounds are reacted in a suitable solvent.

The solvent to be used can be a wide variety of known solvents insofar as they are capable of solving the alkylpyrrolidine of the formula (7) and the compound of the formula (8) and will not adversely affect the reaction. Examples of such solvents are benzene, toluene, xylene and like aromatic hydrocarbons, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, diethyl ether, diisopropyl ether and like ethers, n-hexane, n-heptane and like aliphatic hydrocarbons, cyclohexane and like aliphatic hydrocarbons, etc. Preferable among these solvents are toluene and like aromatic hydrocarbons, chloroform and like hydrocarbon halides and acetone and like ketones. These solvents can be used singly, or at least two of them are usable in admixture. Especially preferable to use are solvents which are free from water (up to 1000 ppm in water content).

The alkylpyrrolidine of the formula (7) and the compound of the formula (8) are used in the ratio usually of 0.5 to 5 moles, preferably 0.9 to 1.2 moles, of the latter per mole of the former.

The reaction of the alkylpyrrolidine of the formula (7) with the compound of the formula (8) is conducted usually at −30 to 100° C., more particularly at −10 to 40° C. The reaction is completed generally in several hours to about 24 hours.

The reaction of the quaternary ammonium salt of the formula (5) obtained above with the compound of the formula (9) is conducted usually by a salt exchange reaction.

The compound of the formula (9) used as a starting material is a known compound. Examples of these are $CF_3CO_2H$, $CF_3CO_2Li$, $CF_3C_2Na$, $CF_3CO_2K$, $CF_3SO_3H$, $CF_3SO_3Li$, $CF_3SO_3Na$, $CF_3SO_3K$, $HN(CF_3SO_2)_2$, $LiN(CF_3SO_2)_2$, $NaN(CF_3SO_2)_2$, $K(CF_3SO_2)_2$, $HN(CF_3CF_2SO_2)_2$, $LiN(CF_3CF_2SO_2)_2$, $NaN(CF_3CF_2SO_2)_2$, $KN(CF_3CF_2SO_2)_2$, $HC(CF_3SO_2)_3$, $LiC(CF_3SO_2)_3$, $NaC(CF_3SO_2)_3$, $KC(CF_3SO_2)_3$, $HN(CF_3SO_2)(CF_3CO)$, $LiN(CF_3SO_2)(CF_3CO)$, $NaN(CF_3SO_2)(CF_3CO)$, $KN(CF_3SO_2)(CF_3CO)$, $HBF_4$, $LiBF_4$, $NaBF_4$, $KBF_4$, $AgBF_4$, $HPF_6$, $LiPF_6$, $NaPF_6$, $KPF_6$ and $AgPF_6$.

This reaction is conducted in a suitable solvent. The solvent to be used can be a wide variety of known solvents insofar as they are capable of dissolving the quaternary ammonium salt of the formula (5) and the compound of the formula (9) and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, ethyl acetate, butyl acetate and like esters, dimethyl sulfoxide, dimethylformamide and like aprotic polar solvents. Preferable among these are methanol and like lower alcohols, chloroform and like hydrocarbon halides and water. These solvents are usable singly, or at least two of them are usable in admixture.

The quaternary ammonium salt of the formula (5) and the compound of the formula (9) are used in the ratio usually of 0.3 to 5 moles, preferably 0.9 to 1.2 moles, of the latter per mole of the former.

The reaction of the quaternary ammonium salt of the formula (5) with the compound of the formula (9) proceeds usually rapidly, so that a solution of the two reactants as dissolved in a solvent is reacted at 5 to 150° C. for about 10 minutes to about 2 hours.

The desired products obtained by the foregoing respective reactions can each be readily isolated from the reaction mixture and purified by usual isolating and purifying means such as centrifuging, concentration, washing, organic solvent extraction, chromatography and recrystallization.

In the case where the product is to be placed into use in which the presence of halogen in the product is objectionable, the amount of halogen present can be diminished by subjecting the halogen salt to neutralization or salt exchange once to remove the halogen, and further converting the product into a salt in conformity with the contemplated use. Examples of useful neutralizing agents are alkali metal salts, alkaline earth metal salts, organic alkali metal salts, silver salts, etc. More specific examples of such agents are sodium carbonate, potassium carbonate, lithium carbonate, calcium carbonate, sodium hydrogencarbonate, potassium hydrogencarbonate, lithium hydrogencarbonate, calcium hydrogencarbonate, sodium hydroxide, potassium hydroxide, lithium hydroxide, calcium hydroxide, sodium perchlorate, potassium perchlorate, lithium perchlorate, sodium acetate, potassium acetate, silver sulfate, silver nitrate, silver perchlorate, etc. The reaction can be carried out in the same mode as the procedure for preparing the quaternary ammonium salt of the formula (1). The dehalogenated intermediate can be represented by the formula (6)

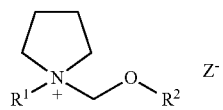

(6)

wherein $R^1$ is straight-chain or branched alkyl having 1 to 4 carbon atoms, $R^2$ is methyl or ethyl, and $Z^-$ is $\frac{1}{2}CO_3^{2-}$, $HCO_3^-$, $\frac{1}{2}SO_4^{2-}$, $ClO_4^-$, $CH_3CO_2^-$ or $OH^-$.

Examples thereof are 1-methoxymethyl-1-methylpyrrolidinium carbonate, 1-methoxymethyl-1-methylpyrrolidinium hydroxide, 1-methoxymethyl-1-methylpyrrolidinium sulfonate, 1-methoxymethyl-1-methylpyrrolidinium perchlorate, 1-methoxymethyl-1-methylpyrrolidinium acetate, 1-methoxymethyl-1-methylpyrrolidinium hydrocarbonate, 1-ethoxymethyl-1-methylpyrrolidinium carbonate, 1-ethoxymethyl-1-methylpyrrolidinium hydroxide, 1-ethoxymethyl-1-methylpyrrolidinium sulfonate, 1-ethoxymethyl-1-methylpyrrolidinium perchlorate, 1-ethoxymethyl-1-methylpyrrolidinium acetate, 1-ethoxymethyl-1-methylpyrrolidinium hydrocarbonate, 1-ethyl-1-methoxymethylpyrrolidinium carbonate, 1-ethyl-1-methoxymethylpyrrolidinium hydroxide, 1-ethyl-1-methoxymethylpyrrolidinium sulfonate, 1-ethyl-1-methoxymethylpyrrolidinium perchlorate, 1-ethyl-1-methoxymethylpyrrolidinium acetate and 1-ethyl-1-methoxymethylpyrrolidinium hydrocarbonate. The procedure for preparing the quaternary ammonium salt of the formula (1) is usable also as the subsequent procedure for converting the dehalogenated salt into a salt in conformity with the contemplated use.

Stated specifically, the quaternary ammonium salt of the formula (1) wherein X is $BF_4$ is prepared from a quaternary ammonium salt of the formula (5) by the reaction procedure to be described below. The quaternary ammonium salt of the formula (5) is dissolved in one of the lower alcohols mentioned above, and a specified amount of a fluoroborate, such as methanol-borofluoric acid or silver borofluoride (for example, up to 70 wt. % in borofluoric acid concentration) is added to the solution to conduct a reaction at 5 to 150° C. for about 30 minutes. The hydrogen halide resulting from the reaction is distilled off, silver halide or like halogen salt is filtered off, and the filtrate is concentrated in a vacuum and dried, whereby the desired compound can be isolated. The hydrogen halide can be removed, for example, by centrifuging, by bubbling of $N_2$ gas while holding the system hot (e.g., at 60 to 150° C.), or by distillation in a vacuum. When the quaternary ammonium salt obtained by the above procedure is to be used as an electrolyte, the water contained will adversely affect the performance of the device, hence there is a need to fully remove the water. The water is removable by bubbling of $N_2$ gas through the system while the system is hot or by distillation in a vacuum, whereas these methods are not limitative. In water content, the salt electrolyte is preferably up to 100 ppm, more preferably up to 50 ppm, further more preferably up to 30 ppm, especially most preferably up to 10 ppm.

The quaternary ammonium salt of the formula (1) wherein X is $N(SO_2CF_3)_2$ is prepared from a quaternary ammonium salt of the formula (5) by the reaction procedure to be described below specifically. The quaternary ammonium salt of the formula (5) is dissolved in water, a specified amount of alkali metal salt of bistrifluoromethanesulfonylimide (lithium salt, sodium salt, potassium salt or like salt of bistrifluoromethanesulfonylimide) is added to the solution, followed by a reaction at 0 to 50° C. for 30 minutes to several hours. The desired product formed is extracted from a suitable solvent (such as dichloromethane, chloroform or ethyl acetate), and the extract is washed with water, then concentrated in a vacuum and dried, whereby the desired product can be isolated. When the quaternary ammonium salt obtained by this procedure is to be used as an electrolyte, the water contained will adversely affect the performance of the device, hence there is a need to fully remove the water. The water is removable by bubbling of $N_2$ gas through the system while holding the system hot or by distillation in a vacuum, whereas these methods are not limitative. In water content, the salt electrolyte is preferably up to 100 ppm, more preferably up to 50 ppm, further more preferably up to 30 ppm, especially most preferably up to 10 ppm.

The quaternary ammonium salt of the formula (1) intended for use in which the presence of halogen in the product is objectionable is prepared by the reaction procedure to be described below specifically. The quaternary ammonium salt of the formula (5) is dissolved in methanol or water, and a specified amount of a metal salt other than halogen salts, such as sodium carbonate or silver sulfate, is added to the solution to effect a reaction at 0 to 50° C. for about 1 hour. The solvent is thereafter concentrated or dried in a vacuum, the residue is dissolved again in a solvent in which the halogenated metal salt formed by the reaction is insoluble and the quaternary ammonium salt is soluble, such as dichloromethane or like halogen solvent, or isopropanol, butanol or like alcohol, and the halogen salt is filtered off. The filtrate is concentrated in a vacuum and dried, whereby a quaternary ammonium salt can be obtained from which the halogen has been predominantly removed. When the desired salt is, for example, a fluorine-containing anion salt, the conversion process to be practiced will be described. The quaternary ammonium salt from which a major portion of halogen salt has been removed is dissolved in water, a specified amount of alkali metal salt of bistrifluoromethanesulfonylimide (lithium salt, sodium salt, potassium salt or like salt of bistrifluoromethanesulfonylimide) or hexafluorophosphoric acid salt (potassium, sodium or lithium hexafluorophosphate) is added to the solution, and the mixture is reacted at 0 to 50° C. for 30 minutes to several hours. The desired product formed is extracted from a suitable solvent (such as dichloromethane, chloroform or ethyl acetate), and the extract is washed with water, thereafter concentrated in a vacuum and dried, whereby the desired product can be obtained in which the halogen content has been reduced to a very small value.

Preparation Process of Equation-2

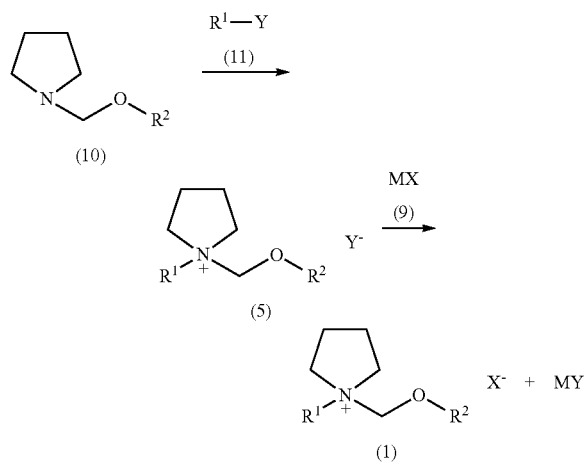

An alkoxypyrrolidine of the formula (10) wherein $R^2$ is the same as above is reacted with a compound of the formula (11) wherein $R^1$ and Y are the same as above to prepare a quaternary ammonium salt of the formula (5), which is then reacted with a compound of the formula (9) wherein M and X are the same as above to thereby prepare a quaternary ammonium salt of the formula (1) wherein X is a group other than Y.

The alkoxypyrrolidine of the formula (10) is reacted with the compound of the formula (11), whereby a quaternary ammonium salt of the formula (5) of the invention is prepared.

The alkoxypyrrolidine of the formula (10) to be used as the starting material is prepared by known processes. Such processes are disclosed, for example, in C. M. McLeod und G. M. Robinson, J. Chem. Soc. 119, 1470 (1921), G. M. Robinson und R. Robinson, J. Chem. Soc. 123, 532 (1923), Stewert, T. D.; Bradly, W. E., J. Am. Chem. Soc. 1932, 54, 4172-4183.

The alkoxypyrrolidine of the formula (10) is prepared generally by using pyrrolidine, formaldehyde or p-formaldehyde, alcohol, and alkali carbonate. Used per mole of pyrrolidine are 0.5 to 3.0 moles, preferably 0.6 to 1.5 moles of formaldehyde or p-formaldehyde, 0.5 to 3.0 moles, preferably 2.0 to 3.0 moles of an alcohol, and 0.2 to 3.0 moles, preferably 0.4 to 1.0 mole of an alkali carbonate. The reaction is conducted at a temperature of −5 to 100° C. and is completed in several hours to about 24 hours. The desired product can be isolated by extraction and rectification.

The compound of the formula (11) is a known compound. Examples of thereof are methyl chloride, methyl bromide, methyl iodide, ethyl iodide, ethyl bromide, n-propyl chloride, n-propyl bromide, n-propyl iodide, iso-propyl chloride, iso-propyl bromide, iso-propyl iodide, n-butyl chloride, n-butyl bromide, n-butyl iodide, iso-butyl chloride, iso-butyl bromide, iso-butyl iodide, tert-butyl chloride, tert-butyl bromide and tert-butyl iodide. The alkoxypyrrolidine of the formula (10) is reacted with the compound of the formula (11) in a suitable solvent.

The solvent to be used can be a wide variety of those already known insofar as they are capable of dissolving the alkoxypyrrolidine of the formula (10) and the compound of the formula (11) and will not adversely affect the reaction. Examples of such solvents are benzene, toluene, xylene and like aromatic hydrocarbons, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, diethyl ether, diisopropyl ether and like ethers, n-hexane, n-heptane and like aliphatic hydrocarbons, cyclohexane and like aliphatic hydrocarbons, etc. Preferable among these solvents are acetone and like ketone, toluene and like aromatic hydrocarbons, and chloroform and like hydrocarbon halides. These solvents can be used singly, or at least two of them are usable in admixture. Especially preferable to use are solvents which are free from water (up to 1000 ppm in water content).

The alkoxypyrrolidine of the formula (10) and the compound of the formula (11) are used in the ratio usually of 0.5 to 5 moles, preferably 0.9 to 1.2 moles, of the latter per mole of the former.

The reaction of the alkoxypyrrolidine of the formula (10) with the compound of the formula (11) is conducted usually at 0 to 150° C. The reaction is completed generally in about 24 hours to about 72 hours. When an alkyl halide having a low boiling point is used for producing the quaternary salt, it is desirable to use an autoclave.

The reaction of the quaternary ammonium salt of the formula (5) obtained above with the compound of the formula (9) is conducted usually by a salt exchange reaction.

This reaction is conducted in a suitable solvent. The solvent to be used can be a wide variety of known solvents insofar as they are capable of dissolving the quaternary ammonium salt of the formula (5) and the compound of the formula (9) and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, ethyl acetate, butyl acetate and like esters, dimethyl sulfoxide, dimethylformamide and like aprotic polar solvents. Preferable among these are methanol and like lower alcohols, chloroform and like hydrocarbon halides and water. These solvents are usable singly, or at least two of them are usable in admixture.

The quaternary ammonium salt of the formula (5) and the compound of the formula (9) are used in the ratio usually of 0.3 to 5 moles, preferably 0.9 to 1.2 moles, of the latter per mole of the former.

The reaction of the quaternary ammonium salt of the formula (5) with the compound of the formula (9) proceeds usually rapidly, so that a solution of the two reactants in a solvent is reacted at about 5 to about 150° C. for about 10 minutes to about 2 hours.

The desired products obtained by the foregoing respective reactions can each be readily isolated from the reaction mixture and purified by usual isolating and purifying means such as centrifuging, concentration, washing, organic solvent extraction, chromatography and recrystallization.

In the case where the product is to be placed into use in which the presence of halogen in the product is objectionable, the amount of halogen present can be diminished by subjecting the halogen salt to neutralization or salt exchange once to remove the halogen, and further converting the product into a salt in conformity with the contemplated use. Examples of useful neutralizing agents are alkali metal salts, alkaline earth metal salts, organic alkali metal salts, silver salts, etc. More specific examples of such agents are sodium carbonate, potassium carbonate, lithium carbonate, calcium carbonate, sodium hydrogencarbonate, potassium hydrogencarbonate, lithium hydrogencarbonate, calcium hydrogencarbonate, sodium hydroxide, potassium hydroxide, lithium hydroxide, calcium hydroxide, sodium perchlorate, potassium perchlorate, lithium perchlorate, sodium acetate, potassium acetate, silver sulfate, silver nitrate, silver perchlorate, etc. The reaction can be carried out in the same mode as the procedure for preparing the quaternary ammonium salt of the formula (1). The dehalogenated intermediate can be represented by the formula (6).

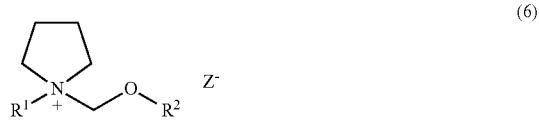

(6)

wherein $R^1$ is straight-chain or branched alkyl having 1 to 4 carbon atoms, $R^2$ is methyl or ethyl, and $Z^-$ is $½CO_3^{2-}$, $HCO_3^-$, $½SO_4^{2-}$, $ClO_4^-$, $CH_3CO_2^-$ or $OH^-$.

Examples thereof are 1-methoxymethyl-1-methylpyrrolidinium carbonate, 1-methoxymethyl-1-methylpyrrolidinium hydroxide, 1-methoxymethyl-1-methylpyrrolidinium sulfonate, 1-methoxymethyl-1-methylpyrrolidinium perchlorate, 1-methoxymethyl-1-methylpyrrolidinium acetate, 1-methoxymethyl-1-methylpyrrolidinium hydrocarbonate, 1-ethoxymethyl-1-methylpyrrolidinium carbonate, 1-ethoxymethyl-1-methylpyrrolidinium hydroxide, 1-ethoxymethyl-1-methylpyrrolidinium sulfonate, 1-ethoxymethyl-1-methylpyrrolidinium perchlorate, 1-ethoxymethyl-1-methylpyrrolidinium acetate, 1-ethoxymethyl-1-methylpyrrolidinium hydrocarbonate, 1-ethyl-1-methoxymethylpyrrolidinium carbonate, 1-ethyl-1-methoxymethylpyrrolidinium hydroxide, 1-ethyl-1-methoxymethylpyrrolidinium sulfonate, 1-ethyl-1-methoxymethylpyrrolidinium perchlorate, 1-ethyl-1-methoxymethylpyrrolidinium acetate and 1-ethyl-1-methoxymethylpyrrolidinium hydrocarbonate. The procedure for preparing the quaternary ammonium salt of the formula (1) is usable also as the subsequent procedure for converting the dehalogenated salt into a salt in conformity with the contemplated use.

Furthermore, the reaction of an alkoxypyrrolidine with an acid ester produces a halogen-free, intermediate. Examples of useful acid esters include carbonic acid esters, sulfuric acid esters, alkyl esters and phosphoric acid esters, among which carbonic acid esters are preferred. Examples of useful carbonic acid esters are dimethyl carbonate, diethyl carbonate, dipropyl carbonate, diisopropyl carbonate, etc. It is usually efficient to conduct the reaction in an autoclave at 50 to 160° C. It is sufficient to conduct the reaction for several hours to about 48 hours.

The halogen-free intermediate can be represented by the formula (12)

(12)

wherein $R^1$ is straight-chain or branched alkyl having 1 to 4 carbon atoms, $R^2$ is methyl or ethyl, and $Q^-$ is $R^1OCO_2^-$.

More specific examples of such intermediates are 1-methoxymethyl-1-methylpyrrolidinium methyl carbonate, 1-ethoxymethyl-1-methylpyrrolidinium methyl carbonate, 1-ethyl-1-methoxymethylpyrrolidinium ethyl carbonate, etc.

Stated specifically, the quaternary ammonium salt of the formula (1) wherein X is $BF_4$ is prepared from a quaternary ammonium salt of the formula (5) by the reaction procedure to be described below. The quaternary ammonium salt of the formula (5) is dissolved in one of the lower alcohols mentioned above, and a specified amount of a fluoroborate, such as methanol-borofluoric acid or silver borofluoride (for example, up to 70 wt. % in borofluoric acid concentration) is added to the solution to conduct a reaction at 5 to 150° C. for about 30 minutes. The hydrogen halide resulting from the reaction is distilled off, silver halide or like halogen salt is filtered off, and the filtrate is concentrated in a vacuum and dried, whereby the desired compound can be isolated. The hydrogen halide can be removed, for example, by centrifuging, by bubbling of $N_2$ gas while holding the system hot (e.g., at 60 to 150° C.), or by distillation in a vacuum. When the quaternary ammonium salt obtained by the above procedure is to be used as an electrolyte, the water contained will adversely affect the performance of the device, hence there is a need to fully remove the water. The water is removable by bubbling of $N_2$ through the system while holding the system hot or by distillation in a vacuum, whereas these methods are not limitative. In water content, the salt electrolyte is preferably up to 100 ppm, more preferably up to 50 ppm, further more preferably up to 30 ppm, especially most preferably up to 10 ppm.

The quaternary ammonium salt of the formula (1) wherein X is $N(SO_2CF_3)_2$ is prepared from a quaternary ammonium salt of the formula (5) by the reaction procedure to be described below specifically. The quaternary ammonium salt of the formula (5) is dissolved in water, a specified amount of alkali metal salt of bistrifluoromethanesulfonylimide (lithium salt, sodium salt, potassium salt or like salt of bistrifluoromethanesulfonylimide) is added to the solution, followed by a reaction at 0 to 50° C. for 30 minutes to several hours. The desired product formed is extracted from a suitable solvent (such as dichloromethane, chloroform or ethyl acetate), and the extract is washed with water, then concentrated in a vacuum and dried, whereby the desired product can be isolated. When the quaternary ammonium salt obtained by this procedure is to be used as an electrolyte, the water contained will adversely affect the performance of the device, hence there is a need to fully remove the water. The water is removable by bubbling of $N_2$ through the system while holding the system hot or by distillation in a vacuum, whereas these methods are not limitative. In water content, the salt electrolyte is preferably up to 100 ppm, more preferably up to 50 ppm, further more preferably up to 30 ppm, especially most preferably up to 10 ppm.

The quaternary ammonium salt of the formula (1) intended for use in which the presence of halogen in the product is objectionable is prepared by the reaction procedure to be described below specifically. The quaternary ammonium salt of the formula (5) is dissolved in methanol or water, and a specified amount of a metal salt other than halogen salts, such as sodium carbonate or silver sulfate, is added to the solution to effect a reaction at 0 to 50° C. for about 1 hour. The solvent is thereafter concentrated or dried in a vacuum, the residue is dissolved again in a solvent in which the halogenated metal salt formed by the reaction is insoluble and the quaternary ammonium salt is soluble, such as dichloromethane or like halogen solvent, or isopropanol, butanol or like alcohol, and the halogen salt is filtered off. The filtrate is concentrated in a vacuum and dried, whereby a quaternary ammonium salt can be obtained from which the halogen has been predominantly removed. When the desired salt is, for example, a fluorine-containing anion salt, the conversion process to be practiced will be described. The quaternary ammonium salt from which a major portion of halogen salt has been removed is dissolved in water, a specified amount of alkali metal salt of bistrifluoromethanesulfonylimide (lithium salt, sodium salt, potassium salt or like salt of bistrifluoromethanesulfonylimide) or hexafluorophosphoric acid salt (potassium, sodium or lithium hexafluorophosphate) is added to the solution, and the mixture is reacted at 0 to 50° C. for 30 minutes to several hours. The desired product formed is extracted from a suitable solvent (such as dichloromethane, chloroform or ethyl acetate), and the extract is washed with water, thereafter concentrated in a vacuum and dried, whereby the desired product can be obtained in which the halogen content has been reduced to a very small value.

The quaternary ammonium salt of the invention or a solution of such a salt as dissolved in an organic solvent is usable as an electrolyte for electrochemical devices such as electric double-layer capacitors or secondary cells.

When the solution of the quaternary ammonium salt as dissolved in an organic solvent is to be used as an electrolyte for electrochemical devices, the concentration of the electrolyte is preferably at least 0.1 M, more preferably at least 0.5 M and most preferably at least 1 M. If the concentration is lower than 0.1 M, the solution is low in electrical conductivity, providing electrochemical devices of impaired performance. The upper limit concentration is the concentration permitting the salt to separate from the organic solvent when the salt is liquid at room temperature. If the salt is free of separation, the upper limit concentration is 100%. When the salt is solid at room temperature, the concentration at which the organic solvent becomes saturated with the salt is the upper limit concentration.

An electrolytic solution for electrochemical devices can be prepared favorably using the quaternary ammonium salt of the invention. The electrolytic solution obtained by the invention is usable for electrochemical devices wherein electric energy can be stored by a physical activity or chemical activity and can be used suitably in electric double-layer capacitors and lithium cells.

A description will be given of a method of preparing an electrolytic solution for use in electric double-layer capacitors using the quaternary ammonium salt of the invention. When the quaternary ammonium of the invention itself is a liquid, the salt is usable as it is as an electrolytic solution, while the salt may be used as mixed with a suitable organic solvent. When the quaternary ammonium salt prepared is to be handled or mixed with an organic solvent, the work is performed in an environment which is not particularly limited insofar as the salt or solution can be free from the atmospheric air since water adversely affects the performance of electric double-layer capacitors, whereas it is desirable to conduct the work within a glove box having an inert atmosphere of argon or nitrogen. The water content of the work environment can be controlled using a dewpoint meter and is preferably up to minus 60° C. When the work environment is in excess of minus 60° C. and if the work is conducted over a prolonged period of time, the electrolyte or electrolytic solution will absorb water from the atmosphere and therefore rises in water content. The water content of the electrolyte or electrolytic solution can be measured by a Karl Fischer meter.

In the case where a solution of the quaternary ammonium salt of the invention in an organic solvent is to be used as the electrolytic solution of electrochemical devices, the concentration of the electrolyte is not limited if it is at least 0.1 M from the viewpoint of electrical conductivity of the solution as previously stated insofar as the electrolyte is free of separation. The electrolyte concentration is preferably at least 0.5 M, more preferably at least 1 M. The upper limit concentration is not defined insofar as no precipitation or separation of the electrolyte occurs. Examples of organic solvents to be used are various as previously mentioned, whereas since the properties such as dielectric constant, viscosity and melting point differ depending on the combination of the quaternary ammonium salt of the invention and the kind of solvent to be mixed therewith, it is desirable to determine the composition of the mixture in accordance with the combination of the quaternary ammonium salt of the invention and the solvent to be mixed therewith for use. For example, in the case of an electrolytic solution comprising N-methoxymethyl-N-methylpyrrolidinium tetrafluoroborate and propylene carbonate, the solution comprises preferably 10 to 80 wt. %, more preferably 15 to 70 wt. %, further more preferably 20 to 60 wt. % of the tetrafluoroborate. In the case of an electrolytic solution comprising N-methoxymethyl-N-methylpyrrolidinium tetrafluoroborate and acetonitrile, the solution comprises preferably 10 to 90 wt. %, more preferably 20 to 70 wt. %, further more preferably 30 to 60 wt. % of the tetrafluoroborate. In the case of an electrolytic solution comprising N-methoxymethyl-N-methylpyrrolidinium tetrafluoroborate and dimethyl carbonate, the solution comprises preferably 40 to 90 wt. %, more preferably 60 to 80 wt. % of the tetrafluoroborate. In the case of an electrolytic solution comprising N-methoxymethyl-N-methylpyrrolidinium tetrafluoroborate and ethylmethyl carbonate, the solution comprises preferably 65 to 90 wt. %, more preferably 65 to 80 wt. % of the tetrafluoroborate. Furthermore organic solvents are usable in admixture. In the case where dimethyl carbonate and ethylmethyl carbonate are used in admixture, the proportion of N-methoxymethyl-N-methylpyrrolidinium tetrafluoroborate is preferably 40 to 80 wt. %.

The quaternary ammonium salt of the invention is usable as an electrolytic solution also for lithium cells. Since water adversely affects the characteristics of lithium cells as when the electrolytic solution of electric double-layer capacitors is prepared, the solution is prepared preferably within a glove box having its dewpoint controlled.

In the case where the quaternary ammonium salt of the invention itself is a liquid, the salt is usable as an electrolytic solution when having a lithium salt dissolved therein. Alternatively, the quaternary ammonium salt of the invention is admixed with a suitable organic solvent, and a lithium salt is dissolved in the mixture for use as an electrolytic solution. The lithium salt to be used can be a wide variety of salts as already mentioned and is not limited particularly insofar as the solution is free of separation of the salt. The concentration of the lithium salt is preferably at least 0.1 M to not higher than 2.0 M, more preferably at least 0.15 M to not higher than 1.5 M, further more preferably at least 0.2 M to not higher than 1.2 M, most preferably at least 0.3 M to not higher than 1.0 M. If the concentration is less than 0.1 M and when the charge-discharge rate is great, depletion of lithium ion occurs in the vicinity of the electrode to result in impaired charge-discharge characteristics. If the lithium ion concentration is over 2.0 M, the electrolytic solution has a high viscosity to entail lower electrical conductivity. It is desired that either one of the two kinds of anions forming the quaternary ammonium salt of the invention and the lithium salt includes $BF_4^-$. Although still remaining to be clarified, the reason appears to be that when the tetrafluoroborate is present, a passive film is formed over the surface of aluminum serving as a positive electrode current collector, inhibiting aluminum from dissolving out. It is desired to adjust the number of $BF_4^-$ anions present to at least 0.5%, preferably at least 0.8%, of the total number of anions in the electrolytic solution. The upper limit for the number of $BF_4^-$ anions to be contained is 100% of the total number of anions in the solution.

The electrolyte of the present invention can be used as diluted with an organic solvent. Examples of organic solvents usable are cyclic carbonic acid esters, chain carbonic acid esters, cyclic ethers, chain ethers, nitrile compounds, sulfone compounds, etc. Examples of cyclic carbonic acid esters are ethylene carbonate, propylene carbonate and the like. Examples of chain carbonic acid esters are dimethyl carbonate, ethylmethyl carbonate and the like. Examples of cyclic ethers are tetrahydrofuran, hexahydropyran and the like. Examples of chain ethers are 1,2-dimethoxyethane and the like. Examples of nitrile compounds are acetonitrile and the like. Examples of sulfone compounds are sulfolane and the like. These solvents can be used in the form of a mixture, such as ethylene carbonate and dimethyl carbonate, ethylene carbonate and ethylmethyl carbonate, ethylene carbonate and propylene carbonate, ethylene carbonate and tetrahydrofuran, etc.

It is desired that the electrolytic solution to be used in the present invention contain at least one of specific organic additives. The term the "specific organic additives" refers to the compounds of the following Formula A, Formula B and Formula C. The reason is that the organic additive incorporated into the solution forms on the surface of the negative electrode of the lithium cell a film known as SEI (solid electrolyte interface) for lithium ions to permeate therethrough selectively, inhibiting the decomposition of ammonium cations which form the salt melting at room temperature or insertion of ammonium cations into the negative electrode material and consequently giving stabilized charge-discharge characteristics. Some kinds of such organic additives are substances also having the function of a diluting organic solvent. Examples of additives having the structure of Formula A are ethylene carbonate, vinylene carbonate, butylene carbonate, etc. Examples of additives having the structure of Formula B are ethylene trithiocarbonate, vinylene trithiocarbonate, etc. Examples of additives having the structure of Formula C are ethylene sulfite, etc. although these examples are not limitative. These additives may be used singly, or at lest two of them are usable in admixture. All the organic additives to be used may be organic additives of Formula A, Formula B and Formula C. At least one of the organic additives of these formulae is used preferably in a proportion preferably of at least 1 wt. % to not greater than 40 wt. %, more preferably at least 1 wt. % to not greater than 30 wt. %, further more preferably at least 1 wt. % to not greater than 20 wt. %, most preferably at least 1 wt. % to not greater than 10 weight %, based on the weight of the entire electrolytic solution. If the proportion is less than 1 wt. %, a satisfactory film will not be formed over the surface of the negative electrode, permitting the decomposition or insertion of the salt melting at room temperature.

$$R^3\text{—}O(CO)\text{—}O\text{—}R^4 \quad \text{Formula A}$$

$$R^5\text{—}S\text{—}(CS)\text{—}S\text{—}R^6 \quad \text{Formula B}$$

$$R^7\text{—}O(SO)\text{—}O\text{—}R^8 \quad \text{Formula C}$$

wherein $R^3$ to $R^8$ are each a saturated hydrocarbon group having 1 to 3 carbon atoms or unsaturated hydrocarbon group having 1 to 3 carbon atoms, and each pair of $R^3$ and $R^4$, $R^5$ and $R^6$, and $R^7$ and $R^8$ may be linked by a single bond, double bond or triple bond to form a ring.

Electric double-layer capacitors can be fabricated favorably using the electrolytic solution of the invention thus obtained. FIG. 7 shows an example of such electric double-layer capacitor. A further description will be given with reference to FIG. 7.

FIG. 7 is a view showing an electric double-layer capacitor of the present invention in section. Indicated at 41 in the drawing is the capacitor, at 42 a first container, at 43 a first electrode, at 44 a second container, at 45 a second electrode, at 46 a partition, at 47 a nonconductive material, and at 48 an electrolytic solution.

The first container 42 is electrically connected to the first electrode 43, and the second container 44 to the second electrode 45. However, the first electrode 42 is separated from the second electrode 45 by the intervening partition 46. Preferably, the first electrode 43 and the second electrode 45 are arranged as opposed to each other.

The first container 42 and the second container 44 are made from a conductive material which will not be corroded with the electrolytic solution 48, such as aluminum, stainless steel or like material. The first electrode 43 and the second electrode 45 to be electrically connected to the respective containers are made from a conductive material. Preferably, these electrodes are made porous so as to have an increased surface area to obtain a high capacity. These electrodes are made preferably from a mixture of a powder of conductive substance and a binder by molding the mixture. Alternatively preferable to use are sheetlike electrodes each made by mixing a powder of conductive substance and a binder with pyrrolidine or like organic solvent to prepare a paste, coating a current collector of aluminum foil with the paste, and drying the coating. Useful conductive substances are activated carbon power, activated carbon fiber and like carbon materials; noble metal oxide materials; conductive high-molecular-weight materials; etc., among which carbon materials are inexpensive and therefore desirable.

The partition 46 to be interposed between the first electrode 43 and the second electrode 45 for separating these electrodes is made from a material which is not limited particularly insofar as the material readily permits the passage of the electrolytic solution therethrough, has insulating properties against the conduction of electrons and is chemically stable. Examples of suitable materials are rayon paper, porous polyolefin film, nonwoven polyethylene fabric, nonwoven polypropylene fabric, cellulose, etc.

The electric double-layer capacitor of the invention is assembled by filling the space between the first container 42 and the second container 44 with the electrolytic solution 48 and sealing off the junction between the containers with the nonconductive material 47 so as not to electrically connect the containers.

The electrolytic solution 48 to be used is one already described above. Preferably, the containers to be filled with the solution are dried in a vacuum, and then filled with the solution 48 within a glove box filled with an inert gas, followed by aging. The containers are dried in a vacuum, preferably with heating at 120 to 300° C., preferably for about 5 to about 100 hours although the time varies with the size of the capacitor. The aging is done to cause the electrodes, especially porous electrodes made from activated carbon or the like, to adsorb ions to the deep portions of the cores to decompose traces of impurities present, preferably by charging the capacitor with voltage of 2 to 3 V at room temperature for about 5 to about 100 hours. It is desirable to finally remove bubbles in a vacuum to complete the electric double-layer capacitor.

With the electric double-layer capacitor of the present invention thus fabricated, the first container 42 and the second container 44 are serviceable at the respective inner sides thereof as current collectors for the first electrode 43 and the second electrode 45, and also serviceable at the respective outer sides thereof as connecting terminals for the first electrode 43 and the second electrode 45.

Lithium secondary cells can be fabricated favorably using the electrolytic solution of the invention thus obtained. Such cells of the invention are in the form of coins, cylinders, rectangular parallelepipeds, laminates, etc. and are not limited particularly in shape. The lithium secondary cell of the invention can be, for example, in the form of a coin as shown in FIG. 9. A further description will be given with reference to FIG. 9. With the coin-shaped cell, a positive electrode and a negative electrode are arranged with a separator provided therebetween, and active substance layers of these positive and negative electrodes and the separator are impregnated with the electrolytic solution. As shown in FIG. 9, the pair of positive electrode and negative electrode and the separator are enclosed along with a spacer and spring inside a positive electrode can and a negative electrode can, which are crimped and sealed off with a gasket provided therebetween.

Examples of positive electrode active substances for use in the present invention are composite oxides of lithium and transition metal or metals, such as $LiCoO_2$, $LiNiO_2$, $LiNi_{1-x}CO_xO_2$, $LiNi_{1-x-y}CO_xMn_y$, $LiNi_{0.5}Mn_{0.5}O_2$, $LiMnO_2$, $LiMn_2O_4$ and $LiNi_{0.5}Mn_{1.5}O_4$, oxides such as $TiO_2$ and $V_2O_5$, sulfides such as $TiS_2$ and $FeS$, etc. From the viewpoint of cell capacity and energy density, composite oxides of lithium and transition metal or metals are desirable. Such a positive electrode active substance can be molded into a positive electrode along with known auxiliary conductive agent and binder under pressure. Alternatively, the positive electrode can be made by mixing the positive electrode active substance with pyrrolidine or like organic solvent along with known conductive agent and binder to prepare a paste, coating a current collector of aluminum foil with the paste and drying the coating.

The negative electrode for use in the present invention can be made from a metal lithium, alloy of metal lithium and other metal, and a material for lithium ions to be inserted thereinto and to be released therefrom. Examples of alloys of metal lithium and other metals are Li—Al, Li—Sn, Li—Zn, Li—Si, etc. Examples of materials for lithium ions to be inserted thereinto and to be released therefrom are carbon materials prepared by firing a resin or pitch, a carbon material obtained by adding a boron compound to such a carbon material, natural graphite, etc. These negative electrode materials can be used singly, or at least two of them are usable in admixture. Such a negative electrode material can be molded into a negative electrode along with known auxiliary conductive agent and binder under pressure. Alternatively, the negative electrode can be made by mixing the negative electrode active substance with pyrrolidine or like organic solvent along with known conductive agent and binder to prepare a paste, coating a current collector of copper foil with the paste and drying the coating.

The separator for use in the invention can be made from a material which is not limited particularly insofar as the material readily passes the electrolytic solution therethrough, has insulating properties and is chemically stable.

The quaternary ammonium salt of the invention and the electrolytic solution containing the salt are high in voltage resistance, electrical conductivity and solubility in organic solvents, and are suitable for use as an electrolytic solution for electrochemical devices. Examples of electrochemical devices are electric double-layer capacitors, secondary cells, solar cells of the pigment sensitizer type, electrochromic devices, condenser, etc., which are nevertheless not limitative. Especially suitable as electrochemical devices are electric double-layer capacitors and secondary cells.

BEST MODE OF CARRYING OUT THE INVENTION

Figure 1:
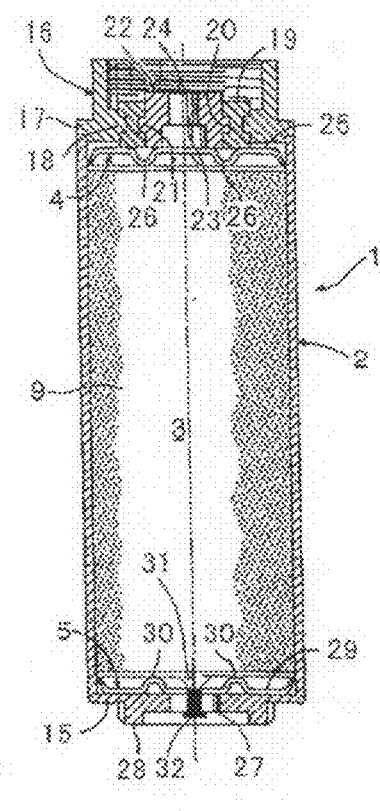
FIG. 1 is a sectional view showing an electric double-layer capacitor of the invention.

The present invention will be described with reference to the following Reference Examples, Examples and Test Examples, but is not limited to these examples.

EXAMPLE 1

Preparation of
N-Methyl-N-Methoxymethylpyrrolidinium Chloride
(N-methoxymethyl-N-methylpyrrolidinium chloride)

A 30.0 g quantity of N-methylpyrrolidine (reagent, product of Tokyo Kasei Co., Ltd.) was dissolved in 120 g of toluene, followed by replacement with nitrogen. Chloromethyl methyl ether (31.2 g, reagent, product of Tokyo Kasei Co., Ltd.) was added dropwise to the solution at 5° C. over a period of 1 hour. The mixture was stirred at 5° C. for 1 hour, then gradually heated to a higher temperature, and stirred at room temperature for 10 hours to complete the reaction. The reaction mixture was filtered, and the resulting solid product was washed with 150 g of toluene and 150 g of acetone. The washed product was dried in a vacuum to obtain 53.7 g of the desired product (white solid).

$^1$H-NMR (D$_2$O) δ ppm: 2.08 (br 4H), 2.96 (s 3H), 3.31 (m 2H), 3.47 (m 2H), 3.55 (s 3H), 4.50 (s 2H)

EXAMPLE 2

Preparation of
N-Methyl-N-Methoxymethylpyrrolidinium
Tetrafluoroborate
(N-methoxymethyl-N-methylpyrrolidinium
Tetrafluoroborate)

A 15.0 g quantity of the N-methyl-N-methoxymethylpyrrolidinium chloride (N-methoxymethyl-N-methylpyrrolidinium chloride) prepared in Example 1 was dissolved in 35 g of MeOH, and 27.83 g of methanol solution of 30% HBF$_4$ was added to the solution. Hydrogen chloride and an excess of HBF$_4$ were removed from the mixture in a vacuum to obtain 19.6 g of the desired product (pale yellow liquid).

$^1$H-NMR (d-DMSO) δ ppm: 2.07 (br 4H), 3.00 (s 3H), 3.42 (m 4H), 3.60 (s 3H), 4.62 (s 2H)

EXAMPLE 3

Preparation of
N-Methyl-N-Methoxymethylpyrrolidinium
Bistrifluoro-Methanesulfonylimide
(N-Methoxymethyl-N-Methylpyrrolidinium
Bistrifluoromethanesulfonylimide)

A 15.0 g quantity of the N-methyl-N-methoxymethylpyrrolidinium chloride (N-methoxymethyl-N-methylpyrrolidinium chloride) prepared in Example 1 was dissolved in 85 g of water, and 26.9 g of lithium bistrifluoromethane-sulfonylimide (reagent, product of Aldrich Corp.) was added to the solution at room temperature. The mixture was stirred for 30 minutes, and chloroform was added to the mixture for extraction. The organic layer was washed with 50 g of water 15 times, thereafter concentrated in a vacuum and dried, giving 33.4 g of the desired product in the form of a colorless liquid.

$^1$H-NMR (d-DMSO) δ ppm: 2.08 (br 4H), 3.00 (s 3H), 3.42 (m 4H), 3.59 (s 3H), 4.63 (s 2H)

EXAMPLE 4

The N-methyl-N-methoxymethylpyrrolidinium tetrafluoroborate (N-methoxymethyl-N-methylpyrrolidinium tetrafluoroborate) prepared in Example 2 was checked for electrical conductivity and voltage resistance.

The electrical conductivity was measured using an electrical conductivity meter (product of Radiometer Analytical SAS). The measuring cell used was CDC641T, product of Radiometer Analytical SAS.

The voltage resistance was measured using a 3-pole electrochemical cell. Used as the working electrode was a glassy carbon electrode (product of BAS Inc.) 1.0 mm in diameter and 0.0079 cm$^{-2}$ in electrode area. The reference electrode used was a silver wire (product of the Nilaco Corp., 99.99% in purity) having a diameter of 0.5 mm. The counter electrode used was a platinum electrode (product of BAS Inc. 11-2233) measuring 0.5 mm in diameter and 50 mm in length. Linear sweep voltammetry was conducted to individually determine the potentials giving an oxidizing current density and reducing current density of 0.5 mAcm$^{-2}$. The difference between the potentials was taken as the voltage resistance. The potential sweep application speed was 50 mVs$^{-1}$. HZ-3000, product of Hokuto Denko Co., Ltd. was used for electrochemical measurement. Table 1 shows the result of measurement.

EXAMPLE 5

The N-methyl-N-methoxymethylpyrrolidinium bistrifluoromethanesulfonylimide (N-methoxymethyl-N-methylpyrrolidinium bistrifluoromethanesulfonylimide) prepared in Example 3 was checked for electrical conductivity and voltage resistance by the same methods as used in Example 4. Table 1 shows the result of measurement.

EXAMPLE 6

The N-methyl-N-methoxymethylpyrrolidinium tetrafluoroborate (N-methoxymethyl-N-methylpyrrolidinium tetrafluoroborate) prepared in Example 2 and propylene carbonate (product of Kishida Chemical Co., Ltd., lithium battery grade) were mixed together to prepare solutions of varying concentrations, which were then checked for electrical conductivity. The conductivity was measured in the same manner as in Example 4. Table 2 shows the results.

EXAMPLE 7

The N-methyl-N-methoxymethylpyrrolidinium tetrafluoroborate (N-methoxymethyl-N-methylpyrrolidinium tetrafluoroborate) prepared in Example 2 and acetonitrile (product of Kishida Chemical Co., Ltd., lithium battery grade) were mixed together to prepare solutions of varying concentrations, which were then checked for electrical conductivity. The conductivity was measured in the same manner as in Example 4. Table 3 shows the results.

EXAMPLE 8

The N-methyl-N-methoxymethylpyrrolidinium bistrifluoromethanesulfonylimide (N-methoxymethyl-N-methylpyrrolidinium bistrifluoromethanesulfonylimide) prepared in Example 3 and propylene carbonate (product of Kishida Chemical Co., Ltd., lithium battery grade) were mixed together to prepare solutions of varying concentrations, which were then checked for electrical conductivity. The conductivity was measured in the same manner as in Example 4. Table 4 shows the results.

COMPARATIVE EXAMPLE 1

Preparation of
N-Methoxyethyl-N-Methylpyrrolidinium
tetrafluoroborate

N-methylpyrrolidine (31.10 g, reagent, product of Tokyo Kasei Co., Ltd.) was dissolved in 124.30 g of toluene, followed by replacement with nitrogen. To the solution was added dropwise 61.22 g of bromoethyl methyl ether (reagent, product of Aldrich Corp.) at 27° C. over a period of 1 hour. The mixture was heated to a gradually raised temperature and then stirred at 60 to 70° C. for 37 hours to terminate the reaction. The reaction mixture was cooled to room temperature, and the resulting solids were filtered off under a nitrogen stream. The filter cake was washed with 70 g of toluene and thereafter dried in a vacuum (giving 78.99 g of a brown solid product). The solid product obtained was suspended in 200 g of acetone, and the suspension was stirred at room temperature, followed by washing with stirring at room temperature and filtration under a nitrogen stream. (This procedure was repeated twice.) The product was dried in a vacuum to result in a yield of 62.64 g. The product, which was colored, was dissolved in 131.83 g of water, 6.00 g of activated carbon (Carboraffin, product of Takeda Pharmaceutical Co., Ltd.) was added to the solution, and the mixture was stirred at 90 to 95° C. for 12 hours. The mixture was cooled to room temperature, and the activated carbon was separated off by filtration. The filtrate was concentrated in a vacuum, followed by drying in a vacuum to result in a yield of 58.34 g. The product was dissolved in a solvent mixture of 200.48 g of acetone and 27.22 g of chloroform with heating for recrystallization. The resulting white solids obtained were filtered off in a nitrogen stream, washed with 50 g of acetone and dried in a vacuum, giving 34.10 g of N-methoxyethyl-N-methylpyrrolidinium bromide.

$^1$H-NMR (CD$_3$OD) δ ppm: 2.24 (m 4H), 3.15 (s 3H), 3.40 (s 3H), 3.65 (m 6H), 3.83 (m 2H)

Subsequently, 40.0 g of the N-methoxyethyl-N-methylpyrrolidinium bromide prepared was dissolved in 40.0 g of MeOH, and 54.0 g of methanol solution of 30 wt. % HBF$_4$ was added to the solution. The mixture was heated at 130° C. in a nitrogen stream to remove hydrogen chloride produced as a by-product and an excess of HBF$_4$, giving 39.9 g of the desired product (white solid).

$^1$H-NMR (CD$_3$OD) δ ppm: 2.22 (m 4H), 3.10 (S 3H), 3.39 (S 3H), 3.58 (m 6H), 3.81 (m 2H)

The N-methyl-N-methoxyethylpyrrolidinium tetrafluoroborate (N-methoxyethyl-N-methylpyrrolidinium tetrafluoroborate) prepared above was checked in the same manner as in Example 4. Table 1 shows the results of measurement.

COMPARATIVE EXAMPLE 2

N-methyl-N-methoxyethylpyrrolidinium bistrifluoromethanesulfonylimide (N-methoxyethyl-N-methylpyrrolidinium bistrifluoromethanesulfonylimide) was prepared and checked in the same manner as in Example 4. Table 1 shows the results of measurement.

COMPARATIVE EXAMPLE 3

Preparation of
N-Methoxymethyl-N-Methylpiperidinium
Tetrafluoroborate

A 54.50 g quantity of N-methylpiperidine (reagent, product of Tokyo Kasei Co., Ltd.) was dissolved in 700 g of dehydrated acetone (reagent, Wako Pure Chemical Ind. Ltd.), followed by replacement with nitrogen. To the solution was added dropwise 44.30 g of chloromethyl methyl ether (reagent, product of Tokyo Kasei Co., Ltd. as purified by distillation) at 5° C. over a period of 1 hour. The mixture was thereafter stirred at a temperature of not higher than 15° C. for 5 hours to terminate the reaction. The reaction mixture was cooled to 5° C., and the resulting solids were filtered off in nitrogen. The filter cake was washed with 400 g of acetone, and thereafter dried in a vacuum. The resulting white solids were suspended in 550 g of acetone, and the suspension was stirred under reflux for 30 minutes. The reaction mixture was filtered, followed by washing with 300 g of acetone. (This procedure was repeated twice.) The resulting solids were dried in a vacuum, giving 66.0 g of the desired product (N-methoxymethyl-N-methylpiperidinium chloride).

$^1$H-NMR (CD$_3$OD) δ ppm: 1.60~1.96 (m 6H), 3.05 (s 3H), 3.35 (m 4H), 3.69 (s 3H), 4.65 (s 2H)

Subsequently, 35.0 g of the N-methoxymethyl-N-methylpiperidinium chloride prepared was dissolved in 35.0 g of MeOH, and 59.9 g of methanol solution of 30 wt. % HBF$_4$ was added to the solution. The mixture was heated at 130° C. in a nitrogen stream to remove hydrogen chloride produced as a by-product, an excess of HBF$_4$ and methanol and obtain 43.7 g of the desired product.

$^1$H-NMR (CD$_3$OD) δ ppm: 1.55~2.00 (m 6H), 3.04 (s 3H), 3.34 (m 4H), 3.67(s 3H), 4.62 (s 2H)

The N-methyl-N-methoxymethylpiperidinium tetrafluoroborate (N-methoxymethyl-N-methylpiperidinium tetrafluoroborate) prepared above was checked in the same manner as in Example 4. Table 1 shows the results of measurement.

COMPARATIVE EXAMPLE 4

N-methyl-N-methoxymethylpiperidinium bistrifluoromethanesulfonylimide (N-methoxymethyl-N-methylpiperidinium bistrifluoromethanesulfonylimide) was prepared and checked in the same manner as in Example 4. Table 1 shows the results of measurement.

COMPARATIVE EXAMPLE 5

Preparation of
N-Methoxymethyl-N-Methylmorpholinium
tetrafluoroborate

A 92.13 g quantity of N-methylmorpholine (reagent, product of Tokyo Kasei Co., Ltd.) was dissolved in 670 g of dehydrated 2-butanone (reagent, product of Wako Pure Chemical Ind. Ltd.), followed by replacement with nitrogen. To the solution was added dropwise 76.47 g of chloromethyl methyl ether (reagent, product of Tokyo Kasei Co., Ltd. as purified by distillation) at 5° C. over a period of 1 hour. The mixture was thereafter stirred at temperature of not higher than 15° C. for 2 hours to terminate the reaction. The reaction mixture was cooled to 5° C., and the resulting solids were filtered off in nitrogen. The filter cake was washed with 500 ml of 2-butanone, and thereafter dried in a vacuum. The resulting white solids were suspended in 500 ml of acetone, and the suspension was stirred under reflux for 30 minutes. The reaction mixture was filtered, followed by washing with 500 ml of acetone. (This procedure was repeated twice.) The resulting solids were dried in a vacuum, affording 150.46 g of the desired product (N-methoxymethyl-N-methylmorpholinium chloride).

$^1$H-NMR (CD$_3$OD) δ ppm: 3.22 (s 3H), 3.36~3.42 (m 2H), 3.52~3.61 (m 2H), 3.71 (s 3H), 4.01 (m 4H), 4.77 (s 2H)

Subsequently, 30.0 g of the N-methoxymethyl-N-methylmorpholinium chloride prepared was dissolved in 30.0 g of MeOH, and 50.8 g of methanol solution of 30 wt. % HBF$_4$ was added to the solution. The mixture was heated at 130° C. in a nitrogen stream to remove hydrogen chloride produced as a by-product, an excess of HBF$_4$ and methanol and obtain 37.2 g of the desired product.

$^1$H-NMR (CD$_3$OD) δ ppm: 3.19 (s 3H), 3.31 (m 2H), 3.52 (m 2H), 3.70 (s 3H), 4.00 (m 4H), 4.72 (s 2H)

The N-methyl-N-methoxymethylmorpholinium tetrafluoroborate (N-methoxymethyl-N-methylmorpholinium tetrafluoroborate) prepared above was used to prepare a 1 M propylene carbonate solution, which was then checked for voltage resistance in the same manner as in Example 4. Table 1 shows the result of measurement.

COMPARATIVE EXAMPLE 6

N-methyl-N-methoxymethylmorpholinium bistrifluoromethanesulfonylimide (N-methoxymethyl-N-methylmorpholinium bistrifluoromethanesulfonylimide) was prepared and checked in the same manner as in Example 4. Table 1 shows the results of measurement.

COMPARATIVE EXAMPLE 7

Preparation of
N-Ethyl-N-Methoxymethyl-N,N-Dimethylammonium Tetrafluoroborate

A 47.50 g quantity of ethyldimethylamine (reagent, product of Tokyo Kasei Co., Ltd.) was dissolved in 300 g of dehydrated acetone (reagent, Wako Pure Chemical Ind. Ltd.), followed by replacement with nitrogen. To the solution was added dropwise 52.30 g of chloromethyl methyl ether (reagent, product of Tokyo Kasei Co., Ltd. as purified by distillation) at 5° C. over a period of 1 hour. The mixture was thereafter stirred at a temperature of not higher than 15° C. for 5 hours to terminate the reaction. The reaction mixture was cooled to 5° C., and the resulting solids were filtered off in nitrogen. The filter cake was washed with 150 g of acetone, and thereafter dried in a vacuum, giving 85.90 g of N-ethyl-N-methoxymethyl-N,N-dimethylammonium chloride (white solid).

$^1$H-NMR (CD$_3$OD) δ ppm: 1.35 (m 3H), 3.03 (s 6H), 3.40 (q 2H), 3.68 (s 3H), 4.61 (s 2H)

Subsequently, 40.0 g of the N-ethyl-N-methoxymethyl-N,N-dimethylammonium chloride prepared was dissolved in 40.0 g of MeOH, and 80.0 g of methanol solution of 30 wt. % HBF$_4$ was added to the solution. The mixture was heated at 130° C. in a nitrogen stream to remove hydrogen chloride produced as a by-product, an excess of HBF$_4$ and methanol and obtain 51.6 g of the desired product.

$^1$H-NMR (CD$_3$OD) δ ppm: 1.34(m 3H), 3.00 (s 6H), 3.38 (q 2H), 3.66 (s 3H), 4.57 (s 2H)

The dimethylethylmethoxymethylammonium tetrafluoroborate (N-ethyl-N-methoxymethyl-N,N-dimethylammonium tetrafluoroborate) prepared above was checked in the same manner as in Example 4. Table 1 shows the result of measurement.

COMPARATIVE EXAMPLE 8

Dimethylethylmethoxymethylammonium bistrifluoromethanesulfonylimide (N-ethyl-N-methoxymethyl-N,N-dimethylammonium bistrifluoromethanesulfonylimide) was prepared and checked in the same manner as in Example 4. Table 1 shows the results of measurement.

COMPARATIVE EXAMPLE 9

Preparation of
N,N-Diethyl-N-Methoxyethyl-N-Methylammonium tetrafluoroborate

Diethylmethylamine (35.53 g, reagent, product of Tokyo Kasei Co., Ltd.) was dissolved in 161.37 g of toluene, followed by replacement with nitrogen. To the solution was added dropwise 68.00 g of bromoethyl methyl ether (reagent, product of Aldrich Corp.) at 27° C. over a period of 1 hour. The mixture was heated to a gradually raised temperature and then stirred at 60 to 70° C. for 44 hours to terminate the reaction. The reaction mixture was cooled to room temperature, and the resulting solids were filtered off in nitrogen. The filter cake was washed with 70 g of toluene and thereafter dried in a vacuum (giving 67.30 g of a brown solid product). The product, which was markedly colored, was dissolved in 131.52 g of water, 7.02 g of activated carbon (Carboraffin, product of Takeda Pharmaceutical Co., Ltd.) was added to the solution, and the mixture was stirred at 90 to 95° C. for 12 hours. The mixture was cooled to room temperature, and the activated carbon was separated off by filtration. The filtrate was concentrated in a vacuum, followed by drying in a vacuum to result in a yield of 58.34 g. The product was dissolved in a solvent mixture of 200.48 g of acetone and 27.22 g of chloroform with heating for recrystallization. The white solids obtained were filtered off in a nitrogen stream, washed with 50 g of acetone and dried in a vacuum, giving 47.58 g of the desired product (N,N-diethyl-N-methoxyethyl-N-methylammonium bromide).

$^1$H-NMR (CD$_3$OD) δ ppm: 1.35 (m 6H), 3.07 (s 3H), 3.39 (s 3H), 3.40~3.57 (m 6H), 3.80 (m 2H)

Subsequently, 30.0 g of the N,N-diethyl-N-methoxyethyl-N-methylammonium bromide prepared was dissolved in 30.0 g of MeOH, and 40.8 g of methanol solution of 30 wt. % HBF$_4$ was added to the solution. The mixture was heated at 130° C. in a nitrogen stream to remove hydrogen chloride produced as a by-product, an excess of HBF$_4$ and methanol, giving 30.2 g of the desired product.

$^1$H-NMR (CD$_3$OD) δ ppm: 1.33 (m 6H), 3.03 (s 3H), 3.38 (s 3H), 3.39~3.52 (m 6H), 3.77 (m 2H)

The diethylmethylmethoxyethylammonium tetrafluoroborate (N,N-diethyl-N-methoxyethyl-N-methylammonium tetrafluoroborate) prepared above was checked in the same manner as in Example 4. Table 1 shows the result of measurement.

COMPARATIVE EXAMPLE 10

Diethylmethylmethoxyethylammonium bistrifluoromethanesulfonylimide (N,N-diethyl-N-methoxyethyl-N-methylammonium bistrifluoromethanesulfonylimide) was prepared and checked in the same manner as in Example 4. Table 1 shows the results of measurement.

COMPARATIVE EXAMPLE 11

Preparation of N,N,N-Triethyl-N-Methylammonium Tetrafluoroborate (TEMA)

A 100 g quantity of triethylmethylammonium chloride (reagent, product of Tokyo Kasei Co., Ltd.) was dissolved in 100 g of methanol, and 200.0 g of a methanol solution of 30 wt. % HBF$_4$ was added to the solution. When the mixture was stirred for 30 minutes, crystals of triethylmethylammonium tetrafluoroborate separated out. The mixture was filtered, and the crystals were washed with isopropyl alcohol and then dried in a nitrogen stream with heating at 130° C. to remove hydrogen chloride produced as a by-product, an excess of HBF$_4$, methanol and isopropyl alcohol, giving 127.1 g of the desired product (white solid).

$^1$H-NMR (CD$_3$OD) δ ppm: 1.31(m 9H), 2.95 (S 3H), 3.34 (q 6H)

The triethylmethylammonium tetrafluoroborate (N,N,N-triethyl-N-methylammonium tetrafluoroborate) prepared above was made into 1 M propylene carbonate solution. The solution was checked for voltage resistance in the same manner as in Example 4. Table 1 shows the result.

COMPARATIVE EXAMPLE 12

The N-methyl-N-methoxyethylpyrrolidinium tetrafluoroborate (N-methoxyethyl-N-methylpyrrolidinium tetrafluoroborate) prepared above and propylene carbonate were mixed together to obtain solutions of varying concentrations, which were then checked for electrical conductivity in the same manner as in Example 4. Table 5 shows the result of measurement.

COMPARATIVE EXAMPLE 13

The N-methyl-N-methoxyethylpyrrolidinium tetrafluoroborate (N-methoxyethyl-N-methylpyrrolidinium tetrafluoroborate) prepared above and acetonitrile were mixed together to obtain solutions of varying concentrations, which were then checked for electrical conductivity in the same manner as in Example 4. Table 6 shows the result of measurement.

COMPARATIVE EXAMPLE 14

The diethylmethylmethoxyethylammonium tetrafluoroborate (N,N-diethyl-N-methoxyethyl-N-methylammonium tetrafluoroborate) prepared above and propylene carbonate were mixed together to obtain solutions of varying concentrations, which were then checked for electrical conductivity in the same manner as in Example 4. Table 7 shows the result of measurement.

COMPARATIVE EXAMPLE 15

The triethylmethylammonium tetrafluoroborate (N,N,N-triethyl-N-methylammonium tetrafluoroborate) prepared above and propylene carbonate were mixed together to obtain solutions of varying concentrations, which were then checked for electrical conductivity in the same manner as in Example 4. Table 8 shows the result of measurement.

COMPARATIVE EXAMPLE 16

The trimethylhexylammonium bistrifluoromethanesulfonylimide (N-hexyl-N,N,N-trimethylammonium bistrifluoromethanesulfonylimide) and propylene carbonate were mixed together to obtain solutions of varying concentrations, which were then checked for electrical conductivity in the same manner as in Example 4. Table 9 shows the result of measurement.

TABLE 1

| | quaternary ammonium salt | | conductivity | | voltage |
|---|---|---|---|---|---|
| | cationic component | nonionic component | state (25° C.) | mScm$^{-1}$ (25° C.) | resistance V |
| Ex. 4 | | BF$_4^-$ | liquid | 7.1 | 6.1 |
| Ex. 5 | | TFSI$^-$ | liquid | 5.4 | 5.7 |
| Com. Ex. 1 | | BF$_4^-$ | liquid | 2.8 | 5.4 |
| Com. Ex. 2 | | TFSI$^-$ | liquid | 3.7 | 5.5 |
| Com. Ex. 3 | | BF$_4^-$ | liquid | 0.9 | 6.0 |
| Com. Ex. 4 | | TFSI$^-$ | liquid | 2.5 | 5.9 |
| Com. Ex. 5 | | BF$_4^-$ | liquid | — | 5.6 |
| Com. Ex. 6 | | TFSI$^-$ | liquid | 1.0 | 6.1 |
| Com. Ex. 7 | | BF$_4^-$ | liquid | 4.4 | 6.1 |
| Com. Ex. 8 | | TFSI$^-$ | liquid | 4.4 | 5.8 |
| Com. Ex. 9 | | BE$_4^-$ | liquid | 1.2 | 5.6 |
| Com. Ex. 10 | | TFSI$^-$ | liquid | 2.5 | 5.8 |
| Com. Ex. 11 | | BF$_4$- | solid | — | 6.0 |

BF$_4^-$ (tetrafluoroborate)
TFSI$^-$ (bistrifluoromethanesulfonylimide)

TABLE 2

Quaternary ammonium salt: N-methyl-N-methoxy-
methylpyrrolidinium tetrafluoroborate (N-methoxy-
methyl-N-methylpyrrolidinium tetrafluoroborate)
Solvent: Propylene carbonate (PC)

| concentration (%) | electrical conductivity mScm$^{-1}$ (25° C.) |
|---|---|
| 0 | 0 |
| 1.8 | 2.1 |
| 8.9 | 8.5 |
| 10 | 9.3 |
| 17.8 | 13.1 |
| 20 | 13.9 |
| 30 | 15.7 |
| 40 | 15.8 |
| 50 | 15.4 |
| 60 | 14.5 |
| 70 | 13.1 |
| 80 | 11.5 |
| 90 | 9.4 |
| 100 | 7.1 |

TABLE 3

Quaternary ammonium salt: N-methyl-N-methoxy-
methylpyrrolidinium tetrafluoroborate (N-
methoxymethyl-N-methylpyrrolidinium tetrafluoroborate)
Solvent: Acetonitrile (AN)

| concentration (%) | electrical conductivity mScm$^{-1}$ (25° C.) |
|---|---|
| 0 | 0 |
| 2.7 | 9.8 |
| 10 | 28.7 |
| 13.2 | 34.7 |
| 20 | 44.5 |
| 25 | 49.7 |
| 30 | 53.9 |
| 40 | 59.1 |
| 50 | 60.1 |
| 60 | 56.2 |
| 70 | 47.5 |
| 80 | 35.1 |
| 90 | 20.8 |
| 100 | 7.1 |

TABLE 4

Quaternary ammonium salt: N-methyl-N-methoxymethylpyrrolidinium
bistrifluoromethanesulfonylimide (N-methoxymethyl-N-
methylpyrrolidinium bistrifluoromethanesulfonylimide)
Solvent: Propylene carbonate (PC)

| concentration (%) | electrical conductivity mScm$^{-1}$ (25° C.) |
|---|---|
| 0 | 0 |
| 3.6 | 1.9 |
| 10 | 5.0 |
| 16.8 | 7.7 |
| 20 | 8.8 |
| 30 | 11.3 |
| 40 | 12.4 |
| 50 | 12.5 |
| 60 | 11.8 |
| 70 | 10.7 |
| 80 | 9.4 |
| 90 | 7.8 |
| 100 | 5.4 |

TABLE 5

Quaternary ammonium salt: N-methyl-N-methoxy-
ethylpyrrolidinium tetrafluoroborate (N-methoxyethyl-
N-methylpyrrolidinium tetrafluoroborate)
Solvent: Propylene carbonate (PC)

| concentration (%) | electrical conductivity mScm$^{-1}$ (25° C.) |
|---|---|
| 0 | 0 |
| 10 | 8.9 |
| 20 | 12.2 |
| 30 | 13.2 |
| 40 | 13.0 |
| 50 | 11.8 |
| 60 | 10.1 |
| 70 | 8.2 |
| 80 | 6.3 |
| 90 | 4.5 |
| 100 | 2.8 |

TABLE 6

Quaternary ammonium salt: N-methyl-N-methoxy-
ethylpyrrolidinium tetrafluoroborate (N-methoxyethyl-
N-methylpyrrolidinium tetrafluoroborate)
Solvent: Acetonitrile (AN)

| concentration (%) | electrical conductivity mScm$^{-1}$ (25° C.) |
|---|---|
| 0 | 0 |
| 10 | 27.2 |
| 20 | 41.7 |
| 30 | 49.2 |
| 40 | 51.9 |
| 50 | 50.3 |
| 60 | 44.8 |
| 70 | 36.0 |
| 80 | 25.3 |
| 90 | 14.1 |
| 100 | 2.8 |

TABLE 7

Quaternary ammonium salt: diethylmethylmethoxy-
ethylammonium tetrafluoroborate (N,N-diethyl-N-
methoxyethyl-N-methylammonium tetrafluoroborate)
Solvent: Propylene carbonate (PC)

| concentration (%) | electrical conductivity mScm$^{-1}$ (25° C.) |
|---|---|
| 0 | 0 |
| 10 | 8.5 |
| 20 | 11.8 |
| 30 | 12.6 |
| 40 | 12.0 |
| 50 | 10.4 |
| 60 | 8.5 |
| 70 | 6.6 |
| 80 | 4.8 |
| 90 | 3.1 |
| 100 | 1.2 |

TABLE 8

Quaternary ammonium salt: triethylmethylammonium tetrafluoroborate
(N,N,N-triethyl-N-methylammonium tetrafluoroborate)
Solvent: Propylene carbonate (PC)

| concentration (%) | electrical conductivity mScm$^{-1}$ (25° C.) |
|---|---|
| 0 | 0 |
| 10 | 10.0 |
| 20 | 14.1 |
| 30 | 15.4 |
| 38 | 15.0 (saturation) |
| 40 | saturation |
| 50 | saturation |
| 60 | saturation |
| 70 | saturation |
| 80 | saturation |
| 90 | saturation |
| 100 | saturation |

TABLE 9

Quaternary ammonium salt: trimethylhexylammonium
bistrifluoromethanesulfonylimide (N-hexyl-N,N,N-
trimethylammonium bistrifluoromethanesulfonylimide)
Solvent: Propylene carbonate (PC)

| concentration (%) | electrical conductivity mScm$^{-1}$ (25° C.) |
|---|---|
| 0 | 0 |
| 10 | 4.3 |
| 20 | 6.9 |
| 30 | 8.3 |
| 40 | 8.6 |
| 50 | 8.2 |
| 60 | 7.1 |
| 70 | 5.6 |
| 80 | 3.8 |
| 90 | 2.2 |
| 100 | 1.0 |

EXAMPLE 9

Preparation of
N-Methoxymethyl-N-Methylpyrrolidinium Chloride

A 50.0 g quantity of N-methylpyrrolidine (reagent, product of Tokyo Kasei Co., Ltd. as purified by rectification and up to 0.1% in both pyrrolidine and water contents) was dissolved in 292.0 g of dehydrated acetone (up to 0.1% in water content), followed by nitrogen replacement. To the solution was added dropwise 47.3 g of chloromethyl methyl ether (reagent, product of Tokyo Kasei Co., Ltd. as purified by distillation) at 5° C. over a period of 1 hour. The mixture was thereafter stirred at 5° C. for 1 hour and then at 5 to not higher than 15° C. for 4 hours to terminate the reaction. The reaction mixture was filtered, and the resulting solids were washed with 120 g of acetone, and dried in a vacuum, affording 92.5 g of the desired product (white solid).

$^1$H-NMR (CD$_3$OD) δ pm: 2.22 (m 4H), 3.11 (s 3H), 3.46 (m 2H), 3.60 (m 2H), 3.67 (s 3H), 4.65 (s 2H)

EXAMPLE 10

Preparation of
N-Methoxymethyl-N-Methylpyrrolidinium Chloride

A 30.0 g quantity of N-methylpyrrolidine (reagent, product of Tokyo Kasei Co., Ltd.) was dissolved in 150 g of toluene, followed by nitrogen replacement. To the solution was added dropwise 31.2 g of chloromethyl methyl ether (reagent, product of Tokyo Kasei Co., Ltd.) at 5° C. over a period of 1 hour. The mixture was stirred at 5° C. for 1 hour, then heated to a gradually elevated temperature and stirred at room temperature for 10 hours to terminate the reaction. The reaction mixture was filtered, and the resulting solids were washed with 150 g of acetone, and dried in a vacuum, affording 53.7 g of a white solid. The quaternary ammonium salt obtained was suspended in 150 g of acetone, followed by stirring for 5 hours, filtration, washing and drying, giving 48.3 g of a white solid. The quaternary ammonium salt obtained was recrystallized from 420 g of chloroform/acetone [1/6(W/W)] and dried in a vacuum, affording 36.2 g of the desired product (white solid).

$^1$H-NMR (CD$_3$OD) δ ppm: 2.22 (m 4H), 3.11 (s 3H), 3.46 (m 2H), 3.60 (m 2H), 3.67 (s 3H), 4.65 (s 2H)

EXAMPLE 11

Preparation of
N-Methoxymethyl-N-Methylpyrrolidinium Bromide

A 17.0 g quantity of N-methylpyrrolidine was dissolved in 160 g of dehydrated acetone (up to 0.1% in water content), followed by nitrogen replacement. To the solution was added dropwise 24.6 g of bromomethyl methyl ether (reagent, product of Tokyo Kasei Co., Ltd.) at 5° C. over a period of 1.5 hours. The mixture was stirred at 5 to not higher than 15° C. for 4 hours to terminate the reaction. The reaction mixture was filtered, and the resulting solids were washed with 160 g of acetone, and dried in a vacuum, affording 30.9 g of the desired product (white solid).

$^1$H-NMR (CD$_3$OD) δ ppm: 2.21 (m 4H), 3.11 (s 3H), 3.48 (m 2H), 3.60 (m 2H), 3.67 (s 3H), 4.65 (s 2H)

EXAMPLE 12

Preparation of
N-Methoxymethyl-N-Methylpyrrolidinium Iodide

A 2.46 g quantity of N-methylpyrrolidine (reagent, product of Tokyo Kasei Co., Ltd. as purified by rectification and up to 0.1% in both pyrrolidine and water contents) was dissolved in 21.74 g of dehydrated 2-butanone (up to 0.1% in water content), followed by nitrogen replacement. To the solution was added dropwise 5.07 g of iodomethyl methyl ether (reagent, product of Aldrich Corp. as purified by rectification) at 5° C. over a period of 1.5 hours. The mixture was stirred at 5 to 15° C. for 5 hours to terminate the reaction. The reaction mixture was filtered, and the filtrate was dried in a vacuum, affording 6.40 g of the desired product (pale reddish brown liquid).

$^1$H-NMR (CD$_3$OD) δ ppm: 2.23 (m 4H), 3.13 (s 3H), 3.50 (m 2H), 3.62 (m 2H), 3.68 (s 3H), 4.68 (s 2H)

EXAMPLE 13

Preparation of
N-Methoxymethyl-N-Methylpyrrolidinium Iodide

A 25.3 g quantity of p-formaldehyde (reagent, product of Wako Pure Chemical Ind. Ltd.) and 58.3 g of potassium carbonate were suspended in 81.0 g of methanol, and 60.0 g of pyrrolidine (reagent, product of Tokyo Kasei Co., Ltd.) was added dropwise to the suspension at room temperature over a period of 1 hour. The mixture was thereafter heated, and reacted at 70° C. for 3 hours. After the reaction, the reaction mixture was cooled to room temperature and filtered. The filtrate was rectified to obtain 68.9 g of a colorless transparent liquid, i.e., methoxymethylpyrrolidine. The pyrrolidine obtained was dissolved in 600 g of acetone, 93.6 g of methyl iodide was added to the solution, and the mixture was stirred at 80° C. for 3 days in an autoclave with the interior atmosphere replaced by nitrogen. The reaction mixture was filtered, and the filtrate was dried in a vacuum, affording 107.3 g of the desired product (reddish brown liquid).

$^1$H-NMR data as to the methoxymethylpyrrolidine $^1$H-NMR (CDCl$_3$) δ ppm: 1.77 (m 4H), 2.76 (m 4H), 3.31 (s 3H), 4.14 (s 2H)

$^1$H-NMR data as to the N-methoxymethyl-N-methylpyrrolidinium iodide $^1$H-NMR (CD$_3$OD) δ ppm: 2.23 (m 4H), 3.13 (s 3H), 3.50 (m 2H), 3.62 (m 2H), 3.68 (s 3H), 4.68 (s 2H)

EXAMPLE 14

Preparation of
N-Methoxymethyl-N-Methylpyrrolidinium
Carbonate

A 1.60 g quantity of sodium carbonate (product of Wako Pure Chemical Ind. Ltd.) was dissolved in 18 g of deionized water, and 5.01 g of N-methoxymethyl-N-methylpyrrolidinium chloride was added to the solution. The mixture was reacted at room temperature for 0.5 hour, whereby the reaction was terminated. The reaction mixture was concentrated and dried in vacuum, and 100 ml of ethyl alcohol was added to the residue to remove insoluble sodium chloride. The resulting product was dissolved in dichloromethane, the solution was filtered with a membrane filter again, and the filtrate was concentrated in a vacuum and dried, giving 5.41 g of the desired product.

$^1$H-NMR (CD$_3$OD) δ ppm: 2.21 (m 4H), 3.11 (s 3H), 3.47 (m 2H), 3.59 (m 2H), 3.67 (s 3H), 4.64 (s 2H)

EXAMPLE 15

Preparation of
N-Methoxymethyl-N-Methylpyrrolidinium
Sulfonate

A 3.14 g quantity of silver sulfate (product of Wako Pure Chemical Ind. Ltd.) was dissolved in 400 ml of deionized water, and 3.34 g of N-methoxymethyl-N-methylpyrrolidinium chloride was added to the solution. The mixture was reacted at room temperature for 0.5 hour, whereby the reaction was completed. The resulting silver chloride was filtered off, and the filtrate was concentrated and dried in a vacuum. The residue was dissolved in methanol, the solution was again filtered with a membrane filter, and the filtrate was concentrated in a vacuum and dried, giving 3.99 g of the desired product.

$^1$H-NMR (CD$_3$OD) δ ppm: 2.21 (m 4H), 3.11 (s 3H), 3.48 (m 2H), 3.61 (m 2H), 3.67 (s 3H), 4.65 (s 2H)

EXAMPLE 16

Preparation of
N-Methoxymethyl-N-Methylpyrrolidinium
Perchlorate

A 5.91 g quantity of sodium perchlorate (product of Wako Pure Chemical Ind. Ltd.) was dissolved in 77 g of ethyl alcohol, and 7.99 g of N-methoxymethyl-N-methylpyrrolidinium chloride was added to the solution. The mixture was reacted at room temperature for 1.5 hours, whereby the reaction was terminated. The resulting sodium chloride was filtered off, and the filtrate was concentrated and dried in a vacuum. The residue was dissolved in dichloromethane, the solution was again filtered with a membrane filter, and the filtrate was concentrated in a vacuum and dried, giving 10.94 g of the desired product.

$^1$H-NMR (CD$_3$OD) δ ppm: 2.21 (m 4H), 3.10 (s 3H), 3.46 (m 2H), 3.58 (m 2H), 3.66 (s 3H), 4.61 (s 2H)

EXAMPLE 17

Preparation of
N-Methoxymethyl-N-Methylpyrrolidinium Fluoride

A 0.44 g quantity of potassium fluoride (product of Wako Pure Chemical Ind. Ltd.) was dissolved in 11 g of deionized water, and 1.74 g of N-methoxymethyl-N-methylpyrrolidinium perchlorate was added to the solution. The mixture was reacted at room temperature for 1.5 hours, whereby the reaction was terminated. With addition of 100 ml of methanol, the reaction mixture was filtered. The filtrate was concentrated and dried in a vacuum. The residue was then dissolved in dichloromethane, the solution was again filtered with a membrane filter, and the filtrate was concentrated and dried, giving 1.05 g of the desired product.

$^1$H-NMR (CD$_3$OD) δ ppm: 2.20 (m 4H), 3.09 (s 3H), 3.46 (m 2H), 3.58 (m 2H), 3.66 (s 3H), 4.60 (s 2H)

EXAMPLE 18

Preparation of
N-Methoxymethyl-N-Methylpyrrolidinium Methyl
carbonate

Methoxymethylpyrrolidine (10.00 g) and 117.39 g of dimethyl carbonate were placed into an autoclave and reacted at 120° C. for 24 hours. The resulting solids were filtered off and washed with dimethyl carbonate. The solids were dried in a vacuum, giving 10.70 g of the desired product.

$^1$H-NMR (CD$_3$OD) δ ppm: 2.21 (m 4H), 3.10 (s 3H), 3.34 (s 3H), 3.45 (m 2H), 3.58 (m 2H), 3.66 (s 3H), 4.62 (s 2H)

EXAMPLE 19

Preparation of
N-Methoxymethyl-N-Methylpyrrolidinium Acetate

A 9.46 g quantity of sodium acetate (product of Wako Pure Chemical Ind. Ltd.) was dissolved in 95 g of methanol, and 19.10 g of N-methoxymethyl-N-methylpyrrolidinium chloride was added to the solution. The mixture was reacted at room temperature for 1.5 hours, whereby the reaction was terminated. The reaction mixture was filtered, and the filtrate was concentrated and dried in a vacuum. To the residue was added 100 ml of dichloromethane, followed by filtration with a membrane filter, concentration in a vacuum and drying, affording 20.38 g of the desired product.

$^1$H-NMR (CD$_3$OD) δ ppm: 1.89 (s 3H), 2.20 (m 4H), 3.10 (s 3H), 3.44 (m 2H), 3.60 (m 2H), 3.66 (s 3H), 4.61 (s 2H)

EXAMPLE 20

Preparation of
N-Methoxymethyl-N-Methylpyrrolidinium
tetrafluoroborate

A 50.0 g quantity of N-methoxymethyl-N-methylpyrrolidinium chloride prepared in Example 9 was dissolved in 120 g of MeOH, and 92.8 g of methanol solution of 30% $HBF_4$ was added to the solution. $N_2$ was bubbled through the mixture with heating at 130° C. to remove hydrogen chloride and an excess of $HBF_4$ and obtain 65.2 g of the desired product (slightly yellow liquid).

$^1$H-NMR ($CD_3OD$) δ ppm: 2.19 (m 4H), 3.08 (s 3H), 3.43 (m 2H), 3.56 (m 2H), 3.65 (s 3H), 4.59 (s 2H)

EXAMPLE 21

Preparation of N-Methoxymethyl-N-Methylpyrrolidinium Bistrifluoromethanesulfonylimide A 5.32 g quantity of N-methoxymethyl-N-methylpyrrolidinium carbonate prepared in Example 14 was dissolved in 24 g of water, and 9.53 g of lithium bistrifluoromethanesulfonylimide (reagent, product of Aldrich Corp.) was added to the solution at room temperature. The mixture was stirred for 30 minutes, and dichloromethane was thereafter added to the mixture, followed by extraction. The organic layer was washed with 50 g of water six times, then concentrated in a vacuum and dried, giving 10.89 g of a colorless liquid as the desired product.

$^1$H-NMR ($CD_3OD$) δ ppm: 2.19 (m 4H), 3.08 (s 3H), 3.42 (m 2H), 3.56 (m 2H), 3.65 (s 3H), 4.57 (s 2H)

EXAMPLE 22

Preparation of N-Methoxymethyl-N-Methylpyrrolidinium bistrifluoromethanesulfonylimide A 2.45 g quantity of N-methoxymethyl-N-methylpyrrolidinium perchlorate prepared in Example 16 was dissolved in 10 g of water, and 3.06 g of lithium bistrifluoromethanesulfonylimide (reagent, product of Aldrich Corp.) was added to the solution at room temperature. The mixture was stirred for 30 minutes, and dichloromethane was thereafter added to the mixture, followed by extraction. The organic layer was washed with 50 g of water six times, then concentrated in a vacuum and dried, giving 3.28 g of a colorless liquid as the desired product.

$^1$H-NMR ($CD_3OD$) δ ppm: 2.19 (m 4H), 3.08 (s 3H), 3.42 (m 2H), 3.56 (m 2H), 3.65 (s 3H), 4.57 (s 2H)

EXAMPLE 23

Preparation of N-Methoxymethyl-N-Methylpyrrolidinium Bistrifluoromethanesulfonylimide A 100 g quantity of methanol was added to 10.50 g of the N-methoxymethyl-N-methylpyrrolidinium methyl carbonate prepared in Example 18, and 14.70 g of bistrifluoromethanesulfonylimide (reagent, product of Aldrich Corp.) was added to the mixture at room temperature. The mixture was stirred for 30 minutes and thereafter concentrated to dryness. Dichloromethane and water were added to the residue, followed by extraction. The organic layer was washed with 100 g of water six times, then concentrated in a vacuum and dried, giving 14.71 g of a colorless liquid as the desired product.

$^1$H-NMR ($CD_3OD$) δ ppm: 2.19 (m 4H), 3.08 (s 3H), 3.42 (m 2H), 3.56 (m 2H), 3.65 (s 3H), 4.57 (s 2H)

EXAMPLE 24

Preparation of N-Methoxymethyl-N-Methylpyrrolidinium trifluoromethanesulfolate

A 30.0 g quantity of N-methoxymethyl-N-methylpyrrolidinium chloride prepared in Example 10 was dissolved in 30.0 g of MeOH, and 80.0 g of methanol solution of 35 wt. % trifluoromethanesulfonic acid was added to the solution. The mixture was heated at 130° C. in a nitrogen stream to remove hydrogen chloride produced as a by-product, an excess of trifluoromethanesulfonic acid and methanol, giving 49.0 g of the desired product.

The compound obtained was checked for electrical conductivity and voltage resistance in the same manner as in Example 4.

$^1$H-NMR ($CD_3OD$) δ ppm: 2.20 (m 4H), 3.09 (s 3H), 3.45 (m 2H), 3.57 (m 2H), 3.66 (s 3H), 4.59 (s 2H)

State (25° C.): liquid,
Conductivity (25° C.): 4.9 $mScm^{-1}$
Voltage resistance: 5.7 V

EXAMPLE 25

Preparation of N-Methoxymethyl-N-Methylpyrrolidinium trifluoroacetate

A 14.94 g quantity of sodium trifluoroacetate was dissolved in 100 g of methanol, and 18.20 g of N-methoxymethyl-N-methylpyrrolidinium chloride was added to the solution at room temperature. The mixture was stirred for 1 hour, concentrated in a vacuum and dried in a vacuum using a vacuum pump. The residue was dissolved in 500 ml of dichloromethane, followed by filtration with a membrane filter, concentration in a vacuum and drying, affording 26.52 g of a colorless liquid as the desired product.

$^1$H-NMR ($CD_3OD$) δ ppm: 2.20 (m 4H), 3.09 (s 3H), 3.43 (m 2H), 3.57 (m 2H), 3.65 (s 3H), 4.59 (s 2H)

EXAMPLE 26

Preparation of N-Methoxymethyl-N-Methylpyrrolidinium hexafluorophosphate

A 20.0 g quantity of N-methoxymethyl-N-methylpyrrolidinium chloride prepared in Example 10 was dissolved in 120 g of water, and 22.2 g of potassium hexafluorophosphate was added to the solution, whereupon a white solid separated out. The mixture was stirred for 30 minutes, and dichloromethane was thereafter added to the mixture for extraction. The organic layer was washed with 120 g of water six times and then dried, affording 25.1 g of a white solid as the desired product.

$^1$H-NMR ($CD_3OD$) δ ppm: 2.19 (m 4H), 3.07 (s 3H), 3.43 (m 2H), 3.55 (m 2H), 3.65 (s 3H), 4.56 (s 2H)

EXAMPLE 27

Preparation of N-Methoxymethyl-N-Methylpyrrolidinium hexafluorophosphate

A 2.85 g quantity of N-methoxymethyl-N-methylpyrrolidinium sulfonate prepared in Example 15 was dissolved in 15 g of water, and 2.65 g of potassium hexafluorophosphate (product of Stella Chemifa Corp.) was added to the solution at room temperature. The mixture was stirred for 1 hour, and dichloromethane was thereafter added to the mixture for extraction. The organic layer was washed with 30 g of water six times, then concentrated in a vacuum and dried in a vacuum, affording 1.51 g of the desired product.

$^1$H-NMR (CD$_3$OD) δ ppm: 2.19 (m 4H), 3.07 (s 3H), 3.43 (m 2H), 3.55 (m 2H), 3.65 (s 3H), 4.56 (s 2H)

EXAMPLE 28

Preparation of
N-Methoxymethyl-N-Methylpyrrolidinium
bis(pentafluoroethanesulfonyl)imide A 15.0 g quantity of N-methoxymethyl-N-methylpyrrolidinium chloride prepared in Example 10 was dissolved in 50 g of water, and 35.1 g of lithium bis(pentafluoroethanesulfonyl)imide was added to the solution. The mixture was stirred for 30 minutes, and dichloromethane was thereafter added to the mixture, followed by extraction. The organic layer was washed with 50 g of water ten times and then dried, giving 31.4 g of a colorless liquid as the desired product.

EXAMPLE 29

Preparation of
N-Ethoxymethyl-N-Methylpyrrolidinium Chloride

A 87.0 g quantity of N-methylpyrrolidine (reagent, product of Tokyo Kasei Co., Ltd. as purified by rectification and up to 0.1% in both pyrrolidine and water contents) was dissolved in 510 g of dehydrated acetone (up to 0.1% in water content), followed by replacement with nitrogen. To the solution was added dropwise 96.6 g of chloromethyl ethyl ether (reagent, product of Tokyo Kasei Co., Ltd. as purified by distillation) at 3° C. over a period of 1 hour. The mixture was stirred at 5° C. for 1 hour and at 5 to not higher than 15° C. for 4 hours to terminate the reaction. The reaction mixture was concentrated, and the concentrate was dried in a vacuum using a vacuum pump. To the residue was added 700 ml of a 2-butanone/acetone solvent mixture (8/2=V/V) for recrystallization at −30° C. The crystals were filtered, washed with a solvent mixture of 2-butanone/acetone and dried in a vacuum, giving 153.1 g of white crystals as the desired product.

$^1$H-NMR (CD$_3$OD) δ ppm: 1.30 (t 3H), 2.23 (m 4H), 3.12 (s 3H), 3.47 (m 2H), 3.60 (m 2H), 3.89 (q 2H), 4.71 (s 2H)

EXAMPLE 30

Preparation of
N-Ethoxymethyl-N-Methylpyrrolidinium
tetrafluoroborate

A 30.0 g quantity of the N-ethoxymethyl-N-methylpyrrolidinium chloride prepared in Example 29 was dissolved in 30.0 g of MeOH, and 51.3 g of methanol solution of 30 wt. % HBF$_4$ was added to the solution. The mixture was heated at 130° C. in a nitrogen stream to remove hydrogen chloride produced as a by-product, an excess of HBF$_4$ and methanol, giving 37.2 g of the desired product.

The compound obtained was checked for electrical conductivity and voltage resistance in the same manner as in Example 4.

$^1$H-NMR (CD$_3$OD) δ ppm: 1.29 (t 3H), 2.20 (m 4H), 3.08 (s 3H), 3.44 (m 2H), 3.56 (m 2H), 3.86 (q 2H), 4.63 (s 2H)

State (25° C.): liquid
Conductivity (25° C.): 5.4 mScm$^{-1}$
Voltage resistance: 6.0 V

EXAMPLE 31

Preparation of
N-Ethoxymethyl-N-Methylpyrrolidinium
bistrifluoromethanesulfonylimide A 15.5 g quantity of N-ethoxymethyl-N-methylpyrrolidinium chloride prepared in Example 29 was dissolved in 92 g of water, and 30.0 g of lithium bistrifluoromethanesulfonylimide (reagent, product of Aldrich Corp.) was added to the solution. The mixture was stirred for 30 minutes, and dichloromethane was then added to the mixture for extraction. The organic layer was washed with 200 g of water six times, then concentrated in a vacuum and dried, giving 31.8 g of a colorless liquid as the desired product.

The compound obtained was checked for electrical conductivity and voltage resistance in the same manner as in Example 4.

$^1$H-NMR (CD$_3$OD) δ ppm: 1.29 (t 3H), 2.21 (m 4H), 3.08 (s 3H), 3.43 (m 2H), 3.56 (m 2H), 3.86 (q 2H), 4.62 (s 2H)

State (25° C.): liquid
Conductivity (25° C.): 5.0 mScm$^{-1}$
Voltage resistance: 5.7 V

EXAMPLE 32

Preparation of
N-Ethyl-N-Methoxymethylpyrrolidinium Chloride

A 34.71 g quantity of N-ethylpyrrolidine (reagent, product of Tokyo Kasei Co., Ltd. as purified by rectification and up to 0.1% in both pyrrolidine and water contents) was dissolved in 189 g of dehydrated acetone (up to 0.1% in water content), followed by replacement with nitrogen. To the solution was added dropwise 28.18 g of chloromethyl ethyl ether (reagent, product of Tokyo Kasei Co., Ltd. as purified by distillation) at 5° C. over a period of 1 hour. The mixture was stirred at 5° C. for 5 hours, whereby the reaction was terminated. The reaction mixture was filtered, washed with 100 g of acetone and dried in a vacuum, giving 50.08 g of a white solid product.

$^1$H-NMR (CD$_3$OD) δ ppm: 1.36 (m 3H), 2.17 (m 4H), 3.41~3.64 (m 6H), 3.64 (s 3H), 4.59 (s 2H)

EXAMPLE 33

Preparation of
N-Ethyl-N-Methoxymethylpyrrolidinium
tetrafluoroborate

A 29.5 g quantity of the N-ethyl-N-methoxymethylpyrrolidinium chloride prepared in Example 32 was dissolved in 30.0 g of MeOH, and 50.4 g of methanol solution of 30 wt. % HBF$_4$ was added to the solution. The mixture was heated at 130° C. in a nitrogen stream to remove hydrogen chloride produced as a by-product, an excess of HBF$_4$ and methanol, giving 36.5 g of the desired product.

$^1$H-NMR (CD$_3$OD) δ ppm: 1.33 (m 3H), 2.16 (m 4H), 3.41~3.62 (m 6H), 3.62 (s 3H), 4.54 (s 2H)

EXAMPLE 34

Preparation of
N-Ethyl-N-Methoxymethylpyrrolidinium
bistrifluoromethanesulfonylimide A 15.38 g quantity of N-ethyl-N-methoxymethylpyrrolidinium chloride prepared in Example 32 was dissolved in 88 g of water, and 30.13 g of lithium bistrifluoromethanesulfonylimide (reagent, product of Aldrich Corp.) was added to the solution at room temperature. The mixture was stirred for 30 minutes, and dichloromethane was thereafter added to the mixture for extraction. The organic layer was washed with 200 g of water seven times, then concentrated in a vacuum and dried, giving 30.5 g of a colorless liquid as the desired product.

$^1$H-NMR (CD$_3$OD) δ ppm: 1.33 (m 3H), 2.16 (m 4H), 3.39~3.62 (m 6H), 3.62 (s 3H), 4.54 (s 2H)

EXAMPLE 35

Preparation of
N-Ethoxymethyl-N-Ethylpyrrolidinium Chloride

A 34.90 g quantity of N-ethylpyrrolidine (reagent, product of Tokyo Kasei Co., Ltd. as purified by rectification and up to 0.1% in both pyrrolidine and water contents) was dissolved in 203 g of dehydrated acetone (up to 0.1% in water content), followed by replacement with nitrogen. To the solution was added dropwise 33.27 g of chloromethyl ethyl ether (reagent, product of Tokyo Kasei Co., Ltd. as purified by distillation) at 5° C. over a period of 1 hour. The mixture was stirred at 5° C. for 5 hours, whereby the reaction was terminated. The reaction mixture was cooled to −30° C., filtered, washed with 100 g of cold acetone and dried in a vacuum, giving 52.10 g of the desired product.

$^1$H-NMR (CD$_3$OD) δ ppm: 1.27~1.37 (m 6H), 2.18 (m 4H), 3.41~3.68 (m 6H), 3.84 (q 2H), 4.64 (s 2H)

EXAMPLE 36

Preparation of
N-Ethoxymethyl-N-Ethylpyrrolidinium
Tetrafluoroborate

A 25.0 g quantity of the N-ethoxymethyl-N-ethylpyrrolidinium chloride prepared in Example 35 was dissolved in 25.0 g of MeOH, and 36.7 g of methanol solution of 30 wt. % HBF$_4$ was added to the solution. The mixture was heated at 130° C. in a nitrogen stream to remove hydrogen chloride produced as a by-product, an excess of HBF$_4$ and methanol, giving 30.4 g of the desired product.

$^1$H-NMR (CD$_3$OD) δ ppm: 1.26~1.36 (m 6H), 2.16 (m 4H), 3.39~3.61 (m 6H), 3.83 (q 2H), 4.59 (s 2H)

EXAMPLE 37

Preparation of
N-Methoxymethyl-N-Propylpyrrolidinium Chloride

A 36.33 g quantity of N-propylpyrrolidine was dissolved in 186 g of dehydrated acetone (up to 0.1% in water content), followed by replacement with nitrogen. To the solution was added dropwise 25.76 g of chloromethyl ethyl ether (reagent, product of Tokyo Kasei Co., Ltd. as purified by distillation) at 5° C. over a period of 1 hour. The mixture was stirred at 5° C. for 5 hours, whereby the reaction was terminated. The reaction mixture was filtered, washed with 100 g of acetone and dried in a vacuum, giving 58.10 g of a white solid product.

$^1$H-NMR (CD$_3$OD) δ ppm: 0.99 (t 3H), 1.76 (m 2H), 2.18 (m 4H), 3.28~3.64 (m 6H), 3.63 (s 3H), 4.58 (s 2H)

EXAMPLE 38

Preparation of
N-Methoxymethyl-N-Propylpyrrolidinium
Tetrafluoroborate

A 28.0 g quantity of the N-methoxymethyl-N-propylpyrrolidinium chloride prepared in Example 37 was dissolved in 28.0 g of MeOH, and 44.4 g of methanol solution of 30 wt. % HBF$_4$ was added to the solution. The mixture was heated at 130° C. in a nitrogen stream to remove hydrogen chloride produced as a by-product, an excess of HBF$_4$ and methanol, giving 34.0 g of the desired product.

$^1$H-NMR (CD$_3$OD) δ ppm: 1.00 (t 3H), 1.75 (m 2H), 2.16 (m 4H), 3.26~3.62 (m 6H), 3.61 (s 3H), 4.54 (s 2H)

EXAMPLE 39

Preparation of
N-Methoxymethyl-N-Propylpyrrolidinium
Bistrifluoromethanesulfonylimide A 15.31 g quantity of N-methoxymethyl-N-propylpyrrolidinium chloride prepared in Example 37 was dissolved in 71 g of water, and 28.01 g of lithium bistrifluoromethanesulfonylimide (reagent, product of Aldrich Corp.) was added to the solution at room temperature. The mixture was stirred for 30 minutes, and dichloromethane was thereafter added to the mixture for extraction. The organic layer was washed with 200 g of water seven times, then concentrated in a vacuum and dried, giving 32.10 g of a colorless liquid as the desired product.

$^1$H-NMR (CD$_3$OD) δ ppm: 1.00 (t 3H), 1.74 (m 2H), 2.16 (m 4H), 3.26~3.61 (m 6H), 3.61 (s 3H), 4.54 (s 2H)

EXAMPLE 40

Preparation of
N-Ethoxymethyl-N-Propylpyrrolidinium Chloride

A 36.22 g quantity of N-propylpyrrolidine was dissolved in 200 g of dehydrated acetone (up to 0.1% in water content), followed by replacement with nitrogen. To the solution was added dropwise 30.25 g of chloromethyl ethyl ether (reagent, product of Tokyo Kasei Co., Ltd. as purified by distillation) at 5° C. over a period of 1 hour. The mixture was stirred at 5° C. for 5 hours, whereby the reaction was terminated. The reaction mixture was filtered, washed with 100 g of acetone and dried in a vacuum, giving 53.30 g of a white solid product.

$^1$H-NMR (CD$_3$OD) δ ppm: 1.01 (t 3H), 1.31 (t 3H), 1.76 (m 2H), 2.18 (br 4H), 3.31 (m 2H), 3.50 (m 2H), 3.61 (m 2H), 3.84 (q 2H), 4.63 (s 2H)

EXAMPLE 41

Preparation of
N-Ethoxymethyl-N-Propylpyrrolidinium
Tetrafluoroborate

A 30.0 g quantity of the N-ethoxymethyl-N-propylpyrrolidinium chloride prepared in Example 40 was dissolved in 30.0 g of MeOH, and 44.4 g of methanol solution of 30 wt. % $HBF_4$ was added to the solution. The mixture was heated at 130° C. in a nitrogen stream to remove hydrogen chloride produced as a by-product, an excess of $HBF_4$ and methanol, giving 35.9 g of the desired product.

$^1$H-NMR ($CD_3OD$) δ ppm: 1.00 (t 3H), 1.28 (t 3H), 1.75 (m 2H), 2.16 (br 4H), 3.29 (m 2H), 3.47 (m 2H), 3.56 (m 2H), 3.82 (q 2H), 4.59 (s 2H)

EXAMPLE 42

Preparation of N-Methoxymethyl-N-Isopropylpyrrolidinium Chloride

A 40.00 g quantity of N-isopropylpyrrolidine was dissolved in 361 g of dehydrated 2-butanone (reagent, product of Wako Pure Chemical Ind. Ltd.), followed by replacement with nitrogen. To the solution was added dropwise 28.76 g of chloromethyl methyl ether (reagent, product of Tokyo Kasei Co., Ltd. as purified by distillation) at 5° C. over a period of 0.5 hour. The mixture was thereafter heated to a gradually elevated temperature and stirred at room temperature for 10 hours, whereby the reaction was terminated. The reaction mixture was cooled to 5° C., and the resulting solids were filtered off in nitrogen. The filter cake was washed with 200 ml of 2-butanone and thereafter dried in a vacuum, giving 66.40 g of the desired product.

$^1$H-NMR ($CD_3OD$) δ ppm: 1.41 (m 6H), 2.15 (m 4H), 3.58 (m 4H), 3.60 (s 3H), 3.84 (m 1H), 4.60 (s 2H)

EXAMPLE 43

Preparation of N-Methoxymethyl-N-Isopropylpyrrolidinium Tetrafluoroborate

A 30.0 g quantity of the N-methoxymethyl-N-isopropylpyrrolidinium chloride prepared in Example 42 was dissolved in 30.0 g of MeOH, and 47.6 g of methanol solution of 30 wt. % $HBF_4$ was added to the solution. The mixture was heated at 130° C. in a nitrogen stream to remove hydrogen chloride produced as a by-product, an excess of $HBF_4$ and methanol, giving 36.7 g of the desired product.

$^1$H-NMR ($CD_3OD$) δ ppm: 1.40 (m 6H), 2.14 (m 4H), 3.54 (m 4H), 3.59 (s 3H), 3.82 (m 1H), 4.57 (s 2H)

EXAMPLE 44

Preparation of N-Methoxymethyl-N-Isopropylpyrrolidinium Bistrifluoromethanesulfonylimide A 15.48 g quantity of N-methoxymethyl-N-isopropylpyrrolidinium chloride prepared in Example 42 was dissolved in 90 g of water, and 27.98 g of lithium bistrifluoromethanesulfonylimide (reagent, product of Aldrich Corp.) was added to the solution at room temperature. The mixture was stirred for 30 minutes, and dichloromethane was thereafter added to the mixture for extraction. The organic layer was washed with 200 g of water ten times, then concentrated in a vacuum and dried, giving 26.84 g of a colorless liquid as the desired product.

$^1$H-NMR ($CD_3OD$) δ ppm: 1.42 (m 6H), 2.13 (m 4H), 3.55 (m 4H), 3.59 (s 3H), 3.82 (m 1H), 4.56 (s 2H)

EXAMPLE 45

Preparation of N-Ethoxymethyl-N-Isopropylpyrrolidinium Chloride

A 40.09 g quantity of N-isopropylpyrrolidine was dissolved in 361 g of dehydrated 2-butanone (reagent, product of Wako Pure Chemical Ind. Ltd.), followed by replacement with nitrogen. To the solution was added dropwise 33.54 g of chloromethyl ethyl ether (reagent, product of Tokyo Kasei Co., Ltd. as purified by distillation) at 5° C. over a period of 0.5 hour. The mixture was thereafter heated to a gradually elevated temperature and stirred at room temperature for 10 hours, whereby the reaction was terminated. The reaction mixture was cooled to 5° C., and the resulting solids were filtered off in nitrogen. The filter cake was washed with 200 ml of 2-butanone, further washed with 200 ml of acetone and dried in a vacuum, giving 55.72 g of the desired product.

$^1$H-NMR ($CD_3OD$) δ ppm: 1.29 (t 3H), 1.43 (m 6H), 2.15 (m 4H), 3.57 (m 4H), 3.83 (q 2H), 3.85 (m 1H), 4.66 (s 2H)

EXAMPLE 46

Preparation of N-Ethoxymethyl-N-Isopropylpyrrolidinium Tetrafluoroborate

A 30.0 g quantity of the N-methoxymethyl-N-isopropylpyrrolidinium chloride prepared in Example 45 was dissolved in 30.0 g of MeOH, and 47.6 g of methanol solution of 30 wt. % $HBF_4$ was added to the solution. The mixture was heated at 130° C. in a nitrogen stream to remove hydrogen chloride produced as a by-product, an excess of $HBF_4$ and methanol, giving 36.7 g of the desired product.

$^1$H-NMR ($CD_3OD$) δ ppm: 1.28 (t 3H), 1.41 (m 6H), 2.14 (m 4H), 3.55 (m 4H), 3.81 (m 3H), 4.62 (s 2H)

COMPARATIVE EXAMPLE 17

Tetraethylammonium Tetrafluoroborate (TEA)

A 120 g quantity of tetraethylammonium bromide (reagent, product of Tokyo Kasei Co., Ltd.) was dissolved in 120 g of methanol, and 172 g of methanol solution of 30 wt. % $HBF_4$ was added to the solution. The mixture was stirred for 30 minutes whereupon crystals of tetraethylammonium tetrafluoroborate separated out. The solution was filtered, the crystals were then washed with isopropyl alcohol, thereafter dried in a nitrogen stream with heating at 130° C. to remove hydrogen bromide produced as a by-product, an excess of $HBF_4$, methanol and isopropyl alcohol, giving 118 g of the desired product (white solid).

$^1$H-NMR ($CD_3OD$) δ ppm: 1.28 (m 12H), 3.29 (q 8H)

EXAMPLE 47

The N-ethoxymethyl-N-methylpyrrolidinium tetrafluoroborate prepared in Example 30 and propylene carbonate (product of Kishida Chemical Co., Ltd., lithium battery grade) were mixed together to obtain solutions of varying concentrations, which were then checked for electrical conductivity in the same manner as in Example 4. Table 10 shows the results of measurement.

EXAMPLE 48

The N-ethyl-N-methoxymethylpyrrolidinium tetrafluoroborate prepared in Example 33 and propylene carbonate

43

(product of Kishida Chemical Co., Ltd., lithium battery grade) were mixed together to obtain solutions of varying concentrations, which were then checked for electrical conductivity in the same manner as in Example 4. Table 11 shows the results of measurement.

EXAMPLE 49

The N-ethoxymethyl-N-ethylpyrrolidinium tetrafluoroborate prepared in Example 36 and propylene carbonate (product of Kishida Chemical Co., Ltd., lithium battery grade) were mixed together to obtain solutions of varying concentrations, which were then checked for electrical conductivity in the same manner as in Example 4. Table 12 shows the results of measurement.

EXAMPLE 50

The N-methoxymethyl-N-propylpyrrolidinium tetrafluoroborate prepared in Example 38 and propylene carbonate (product of Kishida Chemical Co., Ltd., lithium battery grade) were mixed together to obtain solutions of varying concentrations, which were then checked for electrical conductivity in the same manner as in Example 4. Table 13 shows the results of measurement.

EXAMPLE 51

The N-ethoxymethyl-N-propylpyrrolidinium tetrafluoroborate prepared in Example 41 and propylene carbonate (product of Kishida Chemical Co., Ltd., lithium battery grade) were mixed together to obtain solutions of varying concentrations, which were then checked for electrical conductivity in the same manner as in Example 4. Table 14 shows the results of measurement.

EXAMPLE 52

The N-methoxymethyl-N-isopropylpyrrolidinium tetrafluoroborate prepared in Example 43 and propylene carbonate (product of Kishida Chemical Co., Ltd., lithium battery grade) were mixed together to obtain solutions of varying concentrations, which were then checked for electrical conductivity in the same manner as in Example 4. Table 15 shows the results of measurement.

EXAMPLE 53

The N-ethoxymethyl-N-isopropylpyrrolidinium tetrafluoroborate prepared in Example 46 and propylene carbonate (product of Kishida Chemical Co., Ltd., lithium battery grade) were mixed together to obtain solutions of varying concentrations, which were then checked for electrical conductivity in the same manner as in Example 4. Table 16 shows the results of measurement.

EXAMPLE 54

The N-ethoxymethyl-N-methylpyrrolidinium bistrifluoromethanesulfonylimide prepared in Example 31 and propylene carbonate (product of Kishida Chemical Co., Ltd., lithium battery grade) were mixed together to obtain solutions of varying concentrations, which were then checked for electrical conductivity in the same manner as in Example 4. Table 17 shows the results of measurement.

EXAMPLE 55

The N-methoxymethyl-N-propylpyrrolidinium bistrifluoromethanesulfonylimide prepared in Example 39 and propylene carbonate (product of Kishida Chemical Co., Ltd., lithium battery grade) were mixed together to obtain solutions of varying concentrations, which were then checked for electrical conductivity in the same manner as in Example 4. Table 18 shows the results of measurement.

EXAMPLE 56

The N-ethoxymethyl-N-methylpyrrolidinium bistrifluoromethanesulfonylimide prepared in Example 31 and ethylene carbonate/dimethyl carbonate=1/1(V/V) (product of Kishida Chemical Co., Ltd., lithium battery grade) were mixed together to obtain solutions of varying concentrations, which were then checked for electrical conductivity in the same manner as in Example 4. Table 19 shows the results of measurement.

EXAMPLE 57

The N-methoxymethyl-N-propylpyrrolidinium bistrifluoromethanesulfonylimide prepared in Example 39 and ethylene carbonate/dimethyl carbonate=1/1(V/V) (product of Kishida Chemical Co., Ltd., lithium battery grade) were mixed together to obtain solutions of varying concentrations, which were then checked for electrical conductivity in the same manner as in Example 4. Table 20 shows the results of measurement.

TABLE 10

Quaternary ammonium salt: N-ethoxymethyl-N-methylpyrrolidinium tetrafluoroborate (EOMMP-BF$_4$)
Solvent: Propylene carbonate (PC)

| concentration (%) | electrical conductivity mScm$^{-1}$ (25° C.) |
|---|---|
| 0 | 0 |
| 20 | 12.6 |
| 29 | 15.0 |
| 40 | 14.6 |
| 60 | 12.7 |
| 80 | 9.2 |
| 100 | 5.4 |

TABLE 11

Quaternary ammonium salt: N-ethyl-N-methoxymethylpyrrolidinium tetrafluoroborate (EMMP-BF$_4$)
Solvent: Propylene carbonate (PC)

| concentration (%) | electrical conductivity mScm$^{-1}$ (25° C.) |
|---|---|
| 0 | 0 |
| 20 | 12.7 |
| 29 | 15.5 |
| 35 | 15.7 |
| 40 | 15.6 |
| 50 | 15.1 |
| 60 | 13.5 |
| 80 | 9.2 |

TABLE 12

Quaternary ammonium salt: N-ethoxymethyl-N-ethylpyrrolidinium tetrafluoroborate (EEMP-BF$_4$)
Solvent: Propylene carbonate (PC)

| concentration (%) | electrical conductivity mScm$^{-1}$ (25° C.) |
|---|---|
| 0 | 0 |
| 20 | 12.3 |
| 31 | 14.9 |
| 40 | 14.7 |
| 60 | 12.7 |
| 80 | 8.8 |

TABLE 13

Quaternary ammonium salt: N-methoxymethyl-N-propylpyrrolidinium tetrafluoroborate (MMPP-BF$_4$)
Solvent: Propylene carbonate (PC)

| concentration (%) | electrical conductivity mScm$^{-1}$ (25° C.) |
|---|---|
| 0 | 0 |
| 20 | 11.8 |
| 40 | 13.6 |
| 60 | 11.3 |
| 80 | saturation |

TABLE 14

Quaternary ammonium salt: N-ethoxymethyl-N-propylpyrrolidinium tetrafluoroborate (EMPP-BF$_4$)
Solvent: Propylene carbonate (PC)

| concentration (%) | electrical conductivity mScm$^{-1}$ (25° C.) |
|---|---|
| 0 | 0 |
| 20 | 11.5 |
| 40 | 12.9 |
| 60 | 10.4 |
| 80 | 6.5 |

TABLE 15

Quaternary ammonium salt: N-methoxymethyl-N-isopropylpyrrolidinium tetrafluoroborate (MMIP-BF$_4$)
Solvent: Propylene carbonate (PC)

| concentration (%) | electrical conductivity mScm$^{-1}$ (25° C.) |
|---|---|
| 0 | 0 |
| 20 | 8.3 |
| 40 | 13.5 |
| 60 | 10.7 |
| 80 | saturation |

TABLE 16

Quaternary ammonium salt: N-ethoxymethyl-N-isopropylpyrrolidinium tetrafluoroborate (EMIP-BF$_4$)
Solvent: Propylene carbonate (PC)

| concentration (%) | electrical conductivity mScm$^{-1}$ (25° C.) |
|---|---|
| 0 | 0 |
| 20 | 11.4 |
| 40 | 12.9 |
| 60 | 9.9 |
| 80 | saturation |

TABLE 17

Quaternary ammonium salt: N-ethoxymethyl-N-methylpyrrolidinium bistrifluoromethanesulfonylimide (EOMMP-TFSI)
Solvent: Propylene carbonate (PC)

| concentration (%) | electrical conductivity mScm$^{-1}$ (25° C.) |
|---|---|
| 0 | 0 |
| 20 | 8.2 |
| 40 | 11.4 |
| 60 | 11.2 |
| 80 | 8.7 |
| 100 | 5.0 |

TABLE 18

Quaternary ammonium salt: N-methoxymethyl-N-propylpyrrolidinium bistrifluoromethanesulfonylimide (MMPP-TFSI)
Solvent: Propylene carbonate (PC)

| concentration (%) | electrical conductivity mScm$^{-1}$ (25° C.) |
|---|---|
| 0 | 0 |
| 20 | 8.0 |
| 40 | 11.4 |
| 60 | 11.1 |
| 80 | 8.4 |
| 100 | 4.6 |

TABLE 19

Quaternary ammonium salt: N-ethoxymethyl-N-methylpyrrolidinium bistrifluoromethanesulfonylimide (EOMMP-TFSI)
Solvent: ethylene carbonate/dimethyl carbonate [EC/DMC = 1/1(V/V)]

| concentration (%) | electrical conductivity mScm$^{-1}$ (25° C.) |
|---|---|
| 0 | 0 |
| 20 | 12.3 |
| 30 | 15.1 |
| 40 | 16.8 |
| 50 | 16.9 |
| 60 | 16.1 |
| 80 | 11.2 |
| 100 | 5.0 |

TABLE 20

Quaternary ammonium salt: N-methoxymethyl-N-propylpyrrolidinium bistrifluoromethanesulfonylimide (MMPP-TFSI)
Solvent: ethylene carbonate/dimethyl carbonate [EC/DMC = 1/1(V/V)]

| concentration (%) | electrical conductivity mScm$^{-1}$ (25° C.) |
|---|---|
| 0 | 0 |
| 20 | 12.2 |

TABLE 20-continued

Quaternary ammonium salt: N-methoxymethyl-N-propylpyrrolidinium
bistrifluoromethanesulfonylimide (MMPP-TFSI)
Solvent: ethylene carbonate/dimethyl carbonate [EC/DMC = 1/1(V/V)]

| concentration (%) | electrical conductivity mScm$^{-1}$ (25° C.) |
|---|---|
| 30 | 14.9 |
| 40 | 16.5 |
| 50 | 16.6 |
| 60 | 15.3 |
| 80 | 10.5 |
| 100 | 4.6 |

Preparation of Electrolytic Solutions for Electric Double-Layer Capacitors

EXAMPLE 58

MMMP-BF$_4$/PC

The N-methoxymethyl-N-methylpyrrolidinium tetrafluoroborate prepared in Example 20 and propylene carbonate (PC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to −30 ppm in water content. Table 21 shows the concentrations of the solutions.

EXAMPLE 59

MMMP-BF$_4$/EMC

The N-methoxymethyl-N-methylpyrrolidinium tetrafluoroborate prepared in Example 20 and dimethyl carbonate (DMC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 22 shows the concentrations of the solutions.

EXAMPLE 60

MMMP-BF$_4$/EMC

The N-methoxymethyl-N-methylpyrrolidinium tetrafluoroborate prepared in Example 20 and ethylmethyl carbonate (DMC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 23 shows the concentrations of the solutions.

EXAMPLE 61

MMMP-BF$_4$/DMC+EMC

The N-methoxymethyl-N-methylpyrrolidinium tetrafluoroborate prepared in Example 20, dimethyl carbonate (product of Kishida Chemical Co., Ltd., lithium battery grade) and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 24 shows the concentrations of the solutions.

EXAMPLE 62

EOMMP-BF$_4$/EMC

The N-ethoxymethyl-N-methylpyrrolidinium tetrafluoroborate prepared in Example 30 and ethylmethyl carbonate (EMC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 25 shows the concentrations of the solutions.

EXAMPLE 63

EMMP-BF$_4$/EMC

The N-ethyl-N-methoxymethylpyrrolidinium tetrafluoroborate prepared in Example 33 and ethylmethyl carbonate (EMC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 26 shows the concentrations of the solutions.

EXAMPLE 64

EEMP-BF$_4$/EMC

The N-ethoxymethyl-N-ethylpyrrolidinium tetrafluoroborate prepared in Example 36 and ethylmethyl carbonate (EMC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 27 shows the concentrations of the solutions.

EXAMPLE 65

EMPP-BF$_4$/EMC

The N-ethoxymethyl-N-propylpyrrolidinium tetrafluoroborate prepared in Example 41 and ethylmethyl carbonate (EMC) (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 28 shows the concentrations of the solutions.

COMPARATIVE EXAMPLE 18

TEMA-BF$_4$/PC

The N,N,N-triethyl-N-methylammonium tetrafluoroborate prepared in Comparative Example 11 and propylene carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 29 shows the concentrations of the solutions.

COMPARATIVE EXAMPLE 19

TEA-BF$_4$/PC

The tetraethylammonium tetrafluoroborate prepared in Comparative Example 17 and propylene carbonate (product of Kishida Chemical Co., Ltd., lithium battery grade) were mixed together within a dry box having a nitrogen atmosphere, up to −60° C. in dew point, to obtain a solution containing the borate at a concentration of 0.8 M. The solution prepared was found to be up to 30 ppm in water content by a Karl Fischer moisture meter (Hiranuma Moisture Meter AQ-7, product of Hiranuma Sangyo Co., Ltd.). Table 30 shows the concentration of the solution. When the tetraethylammonium tetrafluoroborate was mixed with dimethyl carbonate or ethylmethyl carbonate (product of Kishida Chemical Co., Ltd., lithium battery grade) to varying concentrations, the borate was soluble in neither of the solvents.

COMPARATIVE EXAMPLE 20

EMI-BF$_4$/PC

The 1-ethyl-3-methylimidazolium tetrafluoroborate (EMI-BF$_4$) and propylene carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 31 shows the concentrations of the solutions.

COMPARATIVE EXAMPLE 21

TEMA-BF$_4$/EMC

The N,N,N-triethyl-N-methylammonium tetrafluoroborate prepared in Comparative Example 11 and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 32 shows the concentrations of the solutions.

COMPARATIVE EXAMPLE 22

TEMA-BF$_4$/DMC

The N,N,N-triethyl-N-methylammonium tetrafluoroborate prepared in Comparative Example 11 and dimethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 33 shows the concentrations of the solutions.

COMPARATIVE EXAMPLE 23

EMI-BF$_4$/EMC

The 1-ethyl-3-methylimidazolium tetrafluoroborate and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter-AQ-7, product of Hiranuma Sangyo Co., Ltd.) and found to be up to 30 ppm in water content. Table 34 shows the concentrations of the solutions.

COMPARATIVE EXAMPLE 24

EMI-BF$_4$/DMC

The 1-ethyl-3-methylimidazolium tetrafluoroborate and dimethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 35 shows the concentrations of the solutions.

COMPARATIVE EXAMPLE 25

The N-ethyl-N-methoxymethyl-N,N-dimethylammonium tetrafluoroborate prepared in Comparative Example 7 and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 36 shows the concentrations of the solutions.

COMPARATIVE EXAMPLE 26

The N,N-diethyl-N-methoxyethyl-N-methylammonium tetrafluoroborate prepared in Comparative Example 9 and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 37 shows the concentrations of the solutions.

COMPARATIVE EXAMPLE 27

MMEP-BF$_4$/EMC

The N-methoxyethyl-N-methylpyrrolidinium tetrafluoroborate prepared in Comparative Example 1 and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 38 shows the concentrations of the solutions.

COMPARATIVE EXAMPLE 28

MMMPI-BF$_4$/EMC

The N-methoxymethyl-N-methylpiperidinium tetrafluoroborate (MMMPI-BF$_4$) prepared in Comparative Example 3 and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 39 shows the concentrations of the solutions.

COMPARATIVE EXAMPLE 29

MMMM-BF$_4$/EMC

The N-methoxymethyl-N-methylmorpholinium tetrafluoroborate (MMMM-BF$_4$) prepared in Comparative Example 5 and ethylmethyl carbonate (product of Kishida Chemical Co., Ltd., lithium battery grade) were mixed together within a dry box having a nitrogen atmosphere, up to −60° C. in dew point, to obtain solutions having varying concentrations. The solutions prepared were checked for water content by a Karl Fischer moisture meter (Hiranuma Moisture Meter AQ-7, product of Hiranuma Sangyo Co., Ltd.) and found to be up to 30 ppm in water content. Table 40 shows the concentrations of the solutions.

<Observation of State of Compositions>

The compositions prepared in Examples 58 to 65 and Comparative Examples 18 to 29 were each placed into glass containers having a screw plug inside the dry box, in an amount of 4 cc in each container and brought out of the dry box. The glass containers containing the composition were immersed in a constant-temperature bath and held at 25° C., 0° C. or −30° C. for 5 hours and checked for state visually. The results are shown in Tables 21 to 40, in which "-" indicates separation into two layers, and "solid" represents a solid state.

<Measurement of Electrical Conductivity>

The solution compositions which were found to be in a liquid state free of separation or solidification were brought out of the dry box and checked for electrical conductivity using a conductivity meter (CDM210, product of Radiometer Analytical SAS). The measuring cell used was XE-100 (product of Radiometer Analytical SAS). Tables 21 to 40 show the results.

TABLE 21

| N-methoxymethyl-N-methyl-pyrrolidinium tetrafluoroborate (wt %) | propylene carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 14.5 | 85.5 | 11.8 | 6.7 | 2.3 |
| 17.8 | 82.2 | 13.1 | 7.4 | 2.5 |
| 27 | 73 | 15.4 | 8.4 | 2.6 |
| 35.6 | 64.4 | 15.9 | 8.4 | 2.5 |
| 44.3 | 55.3 | 15.7 | 8.1 | 2.4 |
| 71.0 | 29.0 | 13.0 | 5.7 | 1.3 |

TABLE 22

| N-methoxymethyl-N-methyl-pyrrolidinium tetrafluoroborate (wt %) | dimethyl carbonate (wt %) | conductivity (25° C.) mScm$^{-1}$ | conductivity (0° C.) mScm$^{-1}$ | conductivity (−10° C.) mScm$^{-1}$ | conductivity (−30° C.) mScm$^{-1}$ |
|---|---|---|---|---|---|
| 20 | 80 | — | — | — | — |
| 40 | 60 | 16.5 | solid | solid | solid |
| 60 | 40 | 19.2 | 10.7 | solid | solid |
| 65 | 35 | 18.9 | 10.4 | 7.6 | solid |
| 80 | 20 | 14.9 | 7.1 | 4.9 | 1.6 |

TABLE 23

| N-methoxymethyl-N-methyl-pyrrolidinium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | — | — | — |
| 65 | 35 | 14.8 | 8.1 | 2.5 |
| 80 | 20 | 11.9 | 5.6 | 1.4 |
| 100 wt % | 0 | 7.1 | 2.5 | 0.4 |

TABLE 24

| N-methoxymethyl-N-methyl-pyrrolidinium tetrafluoroborate (wt %) | dimethyl carbonate (wt %) | ethylmethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|---|
| 60 | 10 | 30 | 15.6 | 8.4 | 2.6 |
| 60 | 20 | 20 | 16.9 | 9.1 | 2.8 |
| 60 | 30 | 10 | 18.0 | 9.8 | solid |

TABLE 25

| N-ethoxymethyl-N-methyl-pyrrolidinium tetrafluoroborate (wt %) | ethylmethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | 11.9 | 6.2 | 1.9 |
| 80 | 20 | 9.9 | 4.3 | 1.0 |
| 100 wt % | 0 | 5.4 | 1.8 | 0.2 |

TABLE 26

| N-ethyl-N-methoxymethyl-pyrrolidinium tetrafluoroborate (wt %) | ethylmethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | 13.2 | 6.9 | 0.8 |
| 80 | 20 | 10.6 | solid | solid |

TABLE 27

| N-ethoxymethyl-N-ethyl-pyrrolidinium tetrafluoroborate (wt %) | ethylmethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | 8.8 | 5.3 | 2.1 |
| 60 | 40 | 11.8 | 6.2 | 1.8 |
| 80 | 20 | 9.3 | 3.9 | 0.8 |

TABLE 28

| N-ethoxymethyl-N-propyl-pyrrolidinium tetrafluoroborate (wt %) | ethylmethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | 7.3 | 4.2 | 1.6 |
| 60 | 40 | 9.1 | 4.6 | 1.3 |
| 80 | 20 | 6.7 | 2.5 | solid |

TABLE 29

(TEMA-BF$_4$/PC)

| N,N,N-triethyl-N-methylammonium tetrafluoroborate (wt %) | propylene carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 10 | 90 | 10.0 | 5.6 | 1.9 |
| 20 | 80 | 14.1 | 7.8 | 2.4 |
| 30 | 70 | 15.4 | 7.9 | 2.2 |
| 38 | 62 | 15.0 | 7.6 | solid |

TABLE 30

(TEA-BF$_4$/PC)

| tetraethylammonium tetrafluoroborate (wt %) | propylene carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 14.5 | 85.5 | 12.0 | marked salt precipitation | marked salt precipitation |

TABLE 31

(EMI-BF$_4$/PC)

| ethylmethylimidazolium tetrafluoroborate (wt %) | propylene carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | 15.7 | 8.4 | 2.7 |
| 40 | 60 | 19.8 | 10.3 | 2.8 |
| 60 | 40 | 20.0 | 9.4 | 2.2 |
| 80 | 20 | 18.2 | 7.7 | 1.5 |
| 100 wt % | 0 | 15.3 | 5.9 | solid |

TABLE 32

(TEMA-BF$_4$/EMC)

| N,N,N-triethyl-N-methylammonium tetrafluoroborate (wt %) | ethylmethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| insoluble: 1> | 99< | 0.00003 | — | — |

TABLE 33

(TEMA-BF$_4$/DMC)

| N,N,N-triethyl-N-methylammonium tetrafluoroborate (wt %) | dimethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| insoluble: 1> | 99< | 0.00003 | — | — |

TABLE 34

(EMI-BF$_4$/EMC)

| 1-ethyl-3-methyl-imidazolium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | — | — | — |
| 80 | 20 | 18.6 | 8.7 | 2.1 |
| 100 wt % | 0 | 15.3 | 5.9 | solid |

TABLE 35

(EMI-BF$_4$/DMC)

| 1-ethyl-3-methyl-imidazolium tetrafluoroborate (wt %) | dimethyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | 20.3 | 12.8 | solid |
| 60 | 40 | 25.4 | 13.8 | solid |
| 80 | 20 | 21.9 | 10.5 | 2.6 |
| 100 wt % | 0 | 15.3 | 5.9 | solid |

TABLE 36

| N-ethyl-N-methoxymethyl-N,N-dimethylammonium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | — | — | — |
| 80 | 20 | 10.0 | 3.9 | 0.6 |
| 100 wt % | 0 | 4.4 | 1.0 | 0.1 |

TABLE 37

| N,N-diethyl-N-methoxyethyl-N-methylammonium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | 8.1 | 3.5 | 0.8 |
| 80 | 20 | 4.7 | 1.4 | 0.1 |
| 100 wt % | 0 | 1.2 | 0.2 | solid |

TABLE 38

(MMEP-BF$_4$/EMC)

| N-methoxyethyl-N-methyl-pyrrolidinium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | — | — | — |
| 80 | 20 | 6.6 | 2.4 | 0.4 |
| 100 wt % | 0 | 2.8 | 0.7 | solid |

TABLE 39

(MMMPI-BF$_4$/EMC)

| N-methoxymethyl-N-methyl-pyrrolidinium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | — | — | — |
| 80 | 20 | 4.8 | 1.4 | 0.1 |
| 100 wt % | 0 | 0.9 | 0.1 | solid |

TABLE 40

(MMMM-BF$_4$/EMC)

| N-methoxymethyl-N-methyl-morpholinium tetrafluoroborate (wt %) | ethyl-methyl carbonate (wt %) | conductivity (25° C.) mScm$^{-1}$ | conductivity (0° C.) mScm$^{-1}$ | conductivity (−30° C.) mScm$^{-1}$ |
|---|---|---|---|---|
| 20 | 80 | — | — | — |
| 40 | 60 | — | — | — |
| 60 | 40 | — | — | — |
| 80 | 20 | — | — | — |
| 100 wt % | 0 | solid | solid | solid |

EXAMPLES 66-67 AND COMPARATIVE EXAMPLE 30

<Fabrication of Hollow Cylindrical Electric Double-Layer Capacitors>

FIG. 1 shows a cylindrical electric double-layer capacitor 1 having a closed cylindrical container 2. Enclosed in the closed container 2 are an electrode roll 3, two disklike current collectors 4, 5 and an electrolytic solution.

Figure 2:
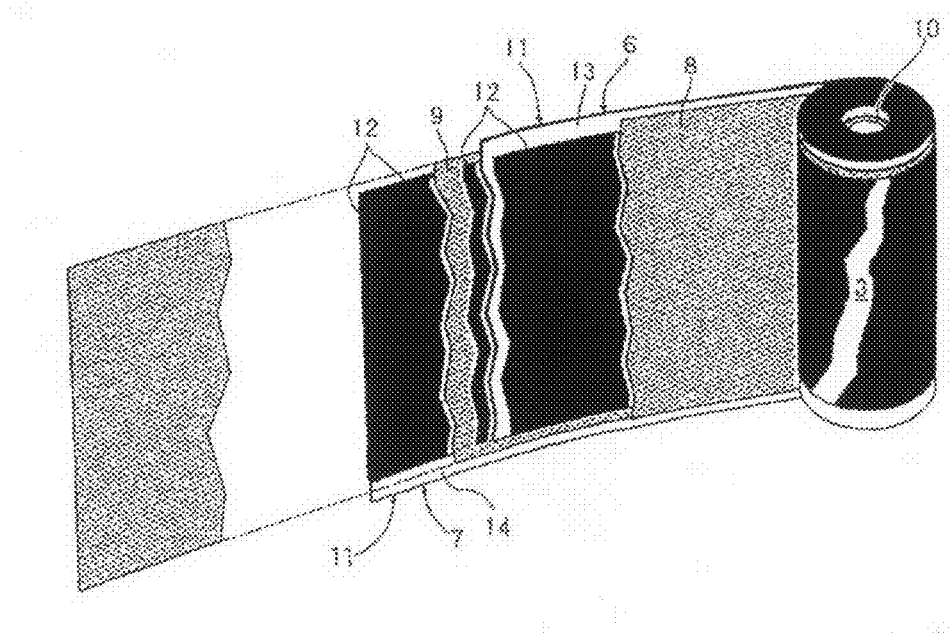
FIG. 2 is a perspective view showing the construction of the capacitor of the invention.

As shown in FIG. 2, the electrode roll 3 comprises a striplike positive electrode 6, a striplike negative electrode 7, and two striplike separators 8, 9 having sandwiched therebetween one of these electrodes 6, 7, i.e., the positive electrode 6 according to the present embodiment, these components 6 to 9 being lapped over one another to form an assembly. The electrode 3 is formed by winding the assembly around an Al core 10 spirally, with one of the separators, 8, on the outer side of the positive electrode 6 located in the innermost position. The other separator 9 between the two electrodes 6, 7 extends outward beyond the outer end of the negative electrode 7 over a length corresponding to approximately one turn of winding so as to cover the outer peripheral portion of the negative electrode 7.

The positive electrode 6 has a striplike current collector 11 and a pair of polarizable electrodes 12 laminated on the respective opposite surfaces of the current collector 11. The current collector 11 has one side edge portion extending longitudinally thereof and providing an electrodeless area over each of opposite surfaces thereof. The electrodeless side edge portion serves as a portion 13 connectable to a positive electrode terminal 22. The negative electrode 7, which is symmetrical to the positive electrode 6 about a point, has a current collector 11, which has one side edge portion extending longitudinally thereof and providing an electrodeless area over each of opposite surfaces thereof. The electrodeless side edge portion serves as a portion 14 connectable to a negative electrode terminal.

With reference to FIG. 1, the closed container 2 comprises a tubular body 15 made of Al and having a bottom, and a closure 16 for closing an opening of the body 15. The closure 16 has an annular outer peripheral plate 17 made of Al and welded to the body 15, an annular intermediate plate 19 made of electrically insulating resin and provided with an outer peripheral groove 18 having fitted therein an inner peripheral edge of the outer peripheral plate 17, and the positive electrode terminal 22 which is tubular and made of an Al alloy and has an outer peripheral ridge 21 fitted in an inner peripheral groove 20 in the intermediate plate 19.

One of the disklike current collectors, 4, which is made of an Al alloy, has at its center a boss 23 fitting in a center bore 24 of the tubular positive electrode terminal 22 and welded thereto. A disk 25 has a plurality of V-shaped ridges 26 arranged radially and projecting downward. The connectable portion 13 of the positive electrode 6 shown in FIG. 2 is welded to the bottoms of the ridges 26.

The other disklike current collector 5, which is made of an Al alloy, has at its center a boss 27 welded to the bottom wall of the tubular body 15 serving as the negative electrode terminal 28. A disk 29 has a plurality of ridges 30 arranged radially and projecting upward. The connectable portion 14 of the negative electrode 7 shown in FIG. 2 is welded to ridgeline portions of the ridges 30.

The electrolytic solution is injected into the closed container 2 through an injection port 31 formed in the boss 27 of the disklike current collector 5 on the negative electrode side. The port 31 is thereafter closed with a rubber plug 32.

Each of the polarizable electrodes 12 shown in FIG. 2 comprises an activated carbon, conductive filler and binder. The materials used were 80 wt. % of activated carbon, 10 wt. % of Ketjen Black EC and 10 wt. % of Teflon 6J (trade name, product of Du Pont-Mitsui Fluorochemical Co., Ltd.), which were kneaded together, and the kneaded mixture was then rolled into an electrode sheet having a thickness of 150 μm. Striplike polarizable electrodes 12, 103 mm in width and 1400 mm in length, were cut out from the electrode sheet. Subsequently, two polarizable electrodes 12 and a striplike current collector 11 in the form of aluminum foil, 109 mm in width, 1400 mm in length and 30 μm in thickness, were pressure-bonded under linear pressure of 6 t using a pair of pressure rollers to make a striplike positive electrode 6. A negative electrode 7 was also made in the same manner as above.

The positive electrode 6, negative electrode 7 and two striplike separators 8, 9 were lapped over one another, with the positive electrode 6 sandwiched between the separators, to obtain an assembly, which was then helically wound around an Al core 10 so that the separator 8 on the outer side of the positive electrode 6 would be located in the innermost position, whereby an electrode roll 3 measuring 38.5 mm in outside diameter D1 and 115 mm in length was prepared.

The electrode roll 3 was placed into a tubular body 15 having a bottom and measuring 39.5 mm in inside diameter D2 and 120 mm in length, and an electrolytic solution was injected into the body 15. The injection port 31 was thereafter closed with a rubber plug 32. Using electrolytic solutions of Examples 59 to 60 and Comparative. Example 18, cylindrical electric double-layer capacitors were fabricated by the procedure described above.

To check the capacitors thus fabricated for durability and reliability, voltage of 2.5 V was continuously applied to the capacitors at 45° C., and the capacitors were thereafter checked for variations in properties as described below.

<Results Achieved by Cylindrical Electric Double-Layer Capacitors>

To check the capacitors fabricated as described above for durability and reliability, voltage of 2.5 V was continuously applied to the capacitors at 45° C. for 1000 hours. The table given below shows the properties of the capacitors thereafter determined.

Figure 3:
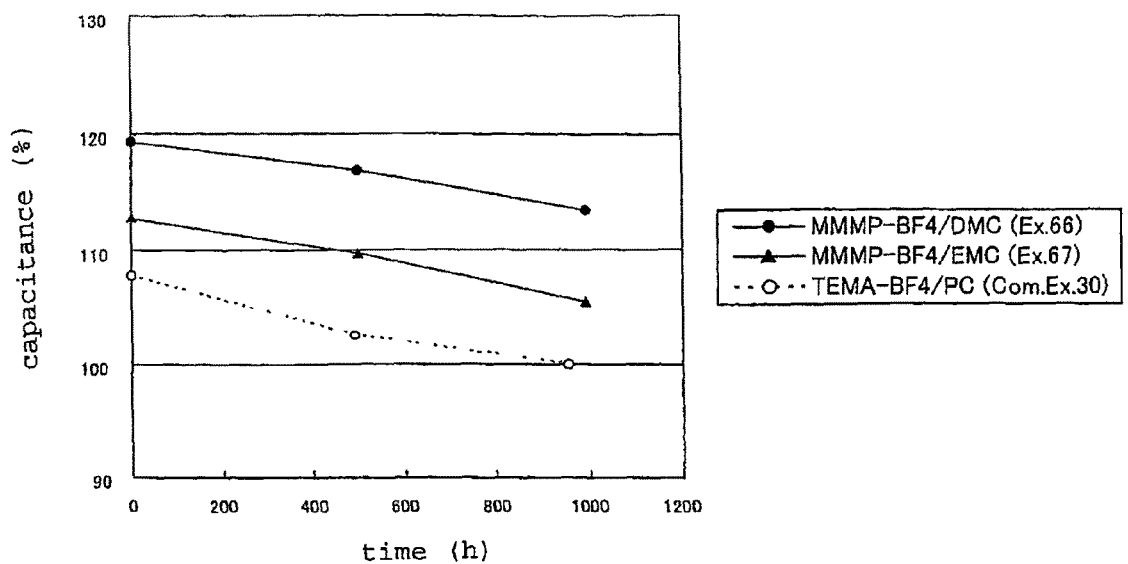
FIG. 3 is a graph showing variations in the capacitance of a cylindrical electric double-layer capacitor when voltage of 2.5 V was continuously applied to the capacitor for 1000 hours.
Figure 4:
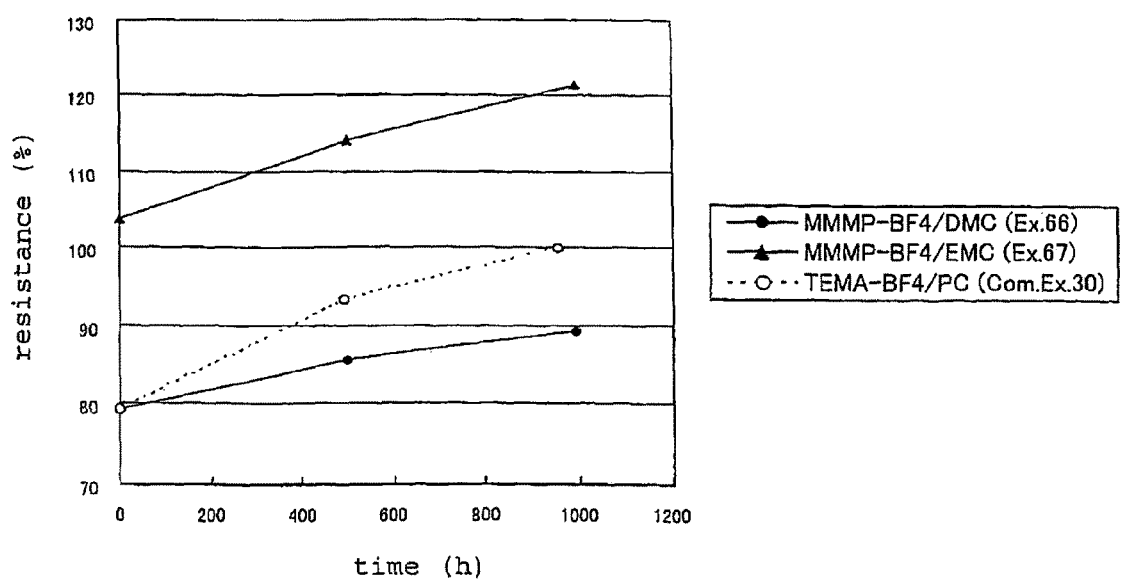
FIG. 4 is a graph showing variations in the resistance of the cylindrical electric double-layer capacitor when voltage of 2.5 V was continuously applied to the capacitor for 1000 hours.
Figure 5:
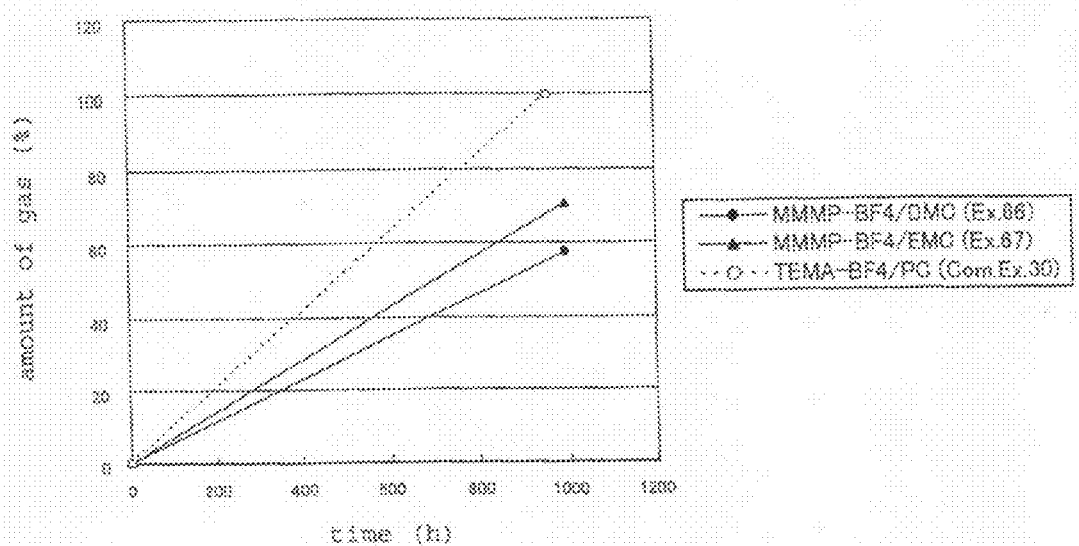
FIG. 5 is a graph showing variations in the amount of gas evolved from the cylindrical electric double-layer capacitor when voltage of 2.5 V was continuously applied to the capacitor for 1000 hours.

In Table 41 and FIGS. 3 to 5, the values of capacitance, resistance and amount of gas evolved are expressed relative to the corresponding values of Comparative Example 30 which are each taken as 100.

TABLE 41

| electric double-layer capacitor | electrolytic solution | composition | capacitance (%) | resistance (%) | gas evolved (%) |
|---|---|---|---|---|---|
| Ex. 66 | Ex. 59 | MMMP-$BF_4$/DMC | 113 | 89 | 57 |
| Ex. 67 | Ex. 60 | MMMP-$BF_4$/EMC | 105 | 121 | 70 |
| Com. Ex. 30 | Com. Ex. 18 | TEMA-$BF_4$/PC | 100 | 100 | 100 |

<Fabrication of Electric Double-Layer Capacitors A>

EXAMPLE 68

Figure 6:
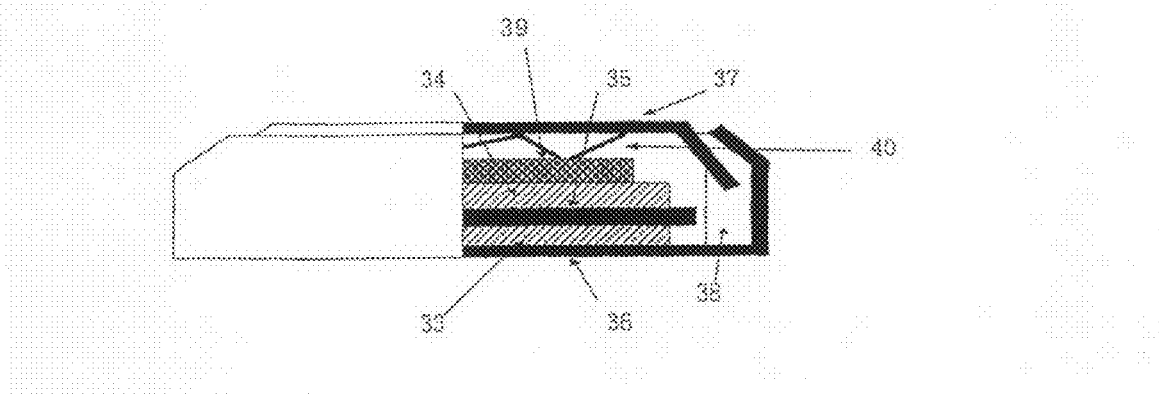
FIG. 6 is a sectional view showing an electric double-layer capacitor having a different construction.

An electric double-layer capacitor A having the construction of FIG. 6 was fabricated using the electrolytic solution prepared in Example 58. Electrodes 33, 34 were made by kneading a conductive substance consisting mainly of activated carbon, binder and N-methylpyrrolidone to prepare a paste, coating aluminum foil with the paste to a thickness of 150 μm, thereafter drying the coating to obtain an electrode sheet and cutting out disks from the sheet. A container 36, container 37, spacer and spring were made of stainless steel, and a separator was made of a nonwoven polypropylene fabric. The capacitor was fabricated inside a glove box filled with argon gas. The electrodes 33, 34, containers 36, 37, spring and spacer were dried in a vacuum with heating at 120° C. for 24 hours and thereafter brought into the glove box. The electrodes 33, 34 and separator were impregnated with the electrolytic solution of Example 58 for use in capacitors of the type mentioned, and the containers 36, 37 were crimped with a gasket provided therebetween to obtain the capacitor of the construction shown in FIG. 6.

COMPARATIVE EXAMPLE 31

An electric double-layer capacitor was fabricated in the same manner as in Example 68 except that the electrolytic solution prepared in Comparative Example 18 was used in place of the electrolytic solution prepared in Example 58 and used in Example 68.

COMPARATIVE EXAMPLE 32

An electric double-layer capacitor was fabricated in the same manner as in Example 68 except that the electrolytic solution prepared in Comparative Example 19 was used in place of the electrolytic solution prepared in Example 58 and used in Example 68.

MEASUREMENT EXAMPLE

The coin-shaped electric double-layer capacitors fabricated in Example 68 and Comparative Examples 31 and 32 were checked for internal resistance and capacitance at 25° C. and −30° C. A coin-shaped cell was set in a holder specific thereto and thereafter immersed in a low constant-temperature bath so as to maintain the cell at a constant temperature. At this time, the holder is covered in its entirety with a vinyl bag so as to hold the cell out of contact with a refrigerant in the bath. The cell was held immersed in the bath as set at the specified temperature for 4 hours and the capacitor was thereafter brought into a charge-discharge operation. The capacitor was charged with constant current at a current density of 2.0 mA, the constant-current charging was changed over to constant-voltage charging upon the voltage reaching 2.5 V, and the capacitor was held at 2.5 V for 120 minutes, followed by constant-current charging at 2.0 mA. Upon the voltage dropping to 0 V, the charging was changed over to low-voltage discharging, and the capacitor was held at 0 V for 120 minutes. The capacitance was calculated from the accumulated value of electric energy discharged. The internal resistance of the cell was calculated from the voltage drop value and the discharge current value immediately after the discharge. Table 42 shows the results of Comparative Examples 31 and 32 relative to the corresponding values of internal resistance and capacitance obtained for Example 68 at 25° C. and −30° C. and taken as 100.

TABLE 42

| Electric double-layer capacitor | electrolytic solution | composition | internal resistance −30° C. | internal resistance 25° C. | capacitance −30° C. | capacitance 25° C. |
|---|---|---|---|---|---|---|
| Ex. 68 | Ex. 58 | 1.5M MMMP-BF$_4$/PC | 100 | 100 | 100 | 100 |
| Com. Ex. 31 | Com. Ex. 18 | 1.5M TEMA-BF$_4$/PC | 122 | 134 | 99 | 89 |
| Com. Ex. 32 | Com. Ex. 19 | 0.8M TEA-BF$_4$/PC | 147 | 192 | 98 | 91 |

<Fabrication of Electric Double-Layer Capacitors B>

EXAMPLE 69

Figure 7:
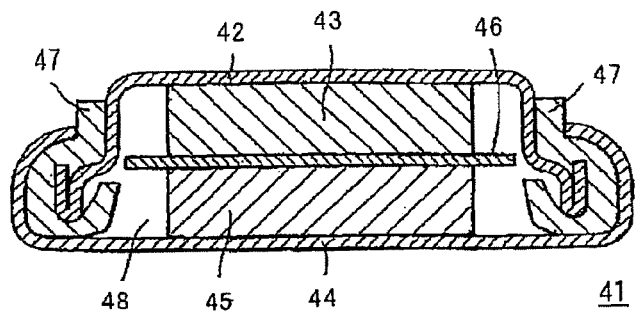
FIG. 7 is a sectional view showing an electric double-layer capacitor having a different construction.

Electric double-layer capacitors B of the construction shown in FIG. 7 were fabricated using the respective electrolytic solutions prepared in Examples 59 to 61. A first electrode 43 and a second electrode 45 were made each by kneading a conductive substance consisting mainly of activated carbon with a binder, and molding the mixture into a disk. The first and second containers 42, 44 were both made of aluminum, and the first and second electrodes 43, 45 were bonded to the respective containers 42, 44 with a conductive adhesive. A partition 46 is rayon paper.

Each capacitor was fabricated by drying in a vacuum the containers of the construction shown in FIG. 7 and above material at 150° C. for 5 hours, and thereafter filling the electrolytic solution into the containers inside a glove box filled with argon gas.

COMPARATIVE EXAMPLES 33-36

Electric double-layer capacitors were obtained in the same manner as in Example 69 except that the electrolytic solutions prepared in Comparative Examples 18, 20, 23 and 24 were used in place of the solutions prepared in Examples 59 to 61.
<Measurement of Reaction Current Values of Electric Double-Layer Capacitors>

Stepwise varying voltages were applied to the capacitors fabricated in Example 69 and Comparative Example 33 using a charge-discharge test device, and the reaction current resulting from the decomposition of the electrolytic solutions was measured at each of the voltage levels to determine the voltage resistance of the electrolytic solutions of Examples 59 to 61 and Comparative Examples 18, 20, 23 and 24.

Figure 8:
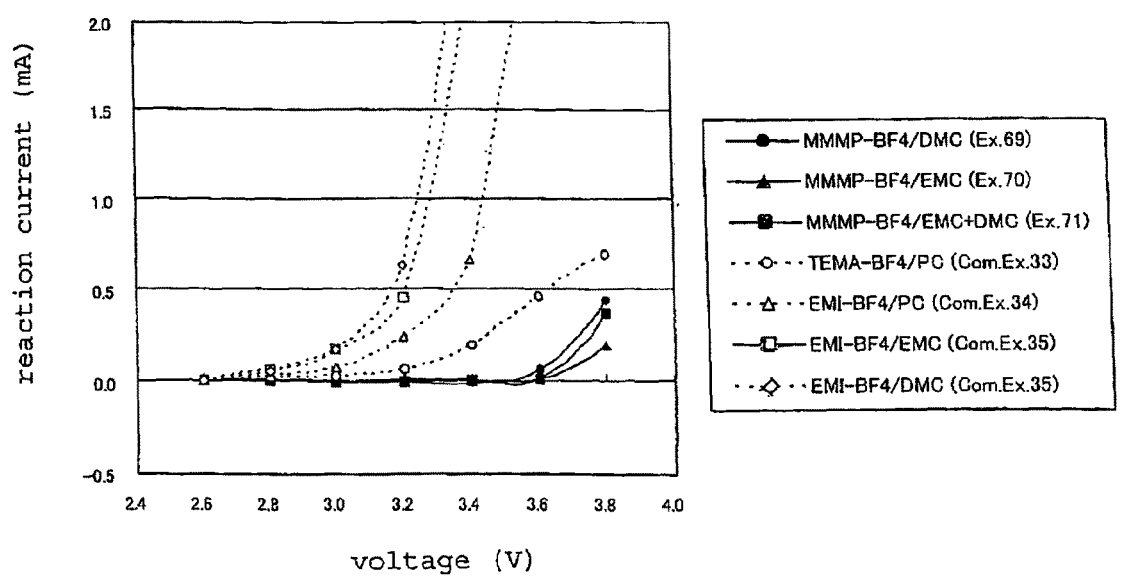
FIG. 8 is a graph showing the relationship between the voltage applied to the capacitor and the reaction current.

Stated more specifically, the capacitor was charged at 25° C. to 2.4 V and thereafter held charged at 2.4 V for 2 hours, and the reaction current value due to the decomposition of the electrolytic solution was measured. The capacitor was then discharged to a predetermined voltage (0.1 V) at a constant current value, then charged to 2.6 V at a constant current value, and thereafter held charged at 2.6 V for 2 hours to measure the resulting reaction current value. The voltage was thereafter raised to 4.0 V stepwise by 0.2 V at each time to measure the resulting reaction current value each time. The voltage at which the reaction current value exceeded 0.1 mA for the first time was taken as the voltage resistance value. FIG. 8 and Table 43 show the results. While the electric double-layer capacitor of the construction described is used at about 2.5 V in actuality, it is known that the higher the voltage resistance value, the higher the long-term durability.

TABLE 43

| electric double-layer capacitor | electrolytic solution | composition | voltage resistance (V) | reaction current at 3.6 V (mA) |
|---|---|---|---|---|
| Ex. 69 | Ex. 59 | MMMP-BF$_4$/DMC | 3.7 | 0.05 |
| Ex. 70 | Ex. 60 | MMMP-BF$_4$/EMC | 3.7 | 0.0 |
| Ex. 71 | Ex. 61 | MMMP-BF$_4$/DMC + EMC | 3.7 | 0.0 |
| Com. Ex. 33 | Com. Ex. 18 | TEMA-BF$_4$/PC | 3.3 | 0.5 |
| Com. Ex. 34 | Com. Ex. 20 | EMI-BF$_4$/PC | 3.1 | 2.5 |
| Com. Ex. 35 | Com. Ex. 23 | EMI-BF$_4$/EMC | 2.9 | 5.0 |

TABLE 43-continued

| electric double-layer capacitor | electrolytic solution | composition | voltage resistance (V) | reaction current at 3.6 V (mA) |
|---|---|---|---|---|
| Com. Ex. 36 | Com. Ex. 24 | EMI-BF$_4$/DMC | 2.9 | 8.1 |

The electric double-layer capacitors fabricated in Examples 69 to 71 produced no reaction current when the voltage was raised to 3.2 or 3.4 V, whereas those fabricated in Comparative Examples 33 to 36 produced reaction current when the voltage exceeded 3.0 V. Furthermore, the capacitors fabricated in Examples 69 to 71 were smaller in reaction current value at all voltage levels.

These results indicate that the electrolytic solutions of Examples 59 to 61 (MMMP-BF$_4$/DMC, MMMP-BF$_4$/EMC, MMMP-BF$_4$/DMC+EMC) were higher in voltage resistance and more excellent in durability than the electrolytic solutions of Comparative Examples 18 and 20 (TEMA-BF$_4$/PC, EMI-BF$_4$/PC) which solutions are generally in use as conventional electrolytic solutions for electric double-layer capacitors. It has also been found that the capacitors of Examples are smaller in reaction current value even at high voltage levels, are therefore diminished in the reduction of capacitance when operated at high voltages and are superior in long-term reliability.

<Preparation of Electrolytic Solutions for Use in Lithium Secondary Cells>

EXAMPLE 72

Lithium tetrafluoroborate (LiBF$_4$) was admixed with the N-methoxymethyl-N-methylpyrrolidinium tetrafluoroborate (MMMP-BF$_4$) obtained in Example 20 at a concentration of 0.6 M. The tetrafluoroborates were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

EXAMPLE 73

Lithium bis(trifluoromethanesulfonyl)imide (LiTFSI) was admixed with the N-methoxymethyl-N-methylpyrrolidinium bis(trifluoromethanesulfonyl)imide (MMMP-TFSI) obtained in Example 3 at a concentration of 0.6 M. The imides were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

EXAMPLE 74

Lithium bis(trifluoromethanesulfonyl)imide (LiTFSI) and lithium tetrafluoroborate (LiBF$_4$) were admixed at respective concentrations of 0.4 M and 0.2 M with the N-methoxymethyl-N-methylpyrrolidinium bis(trifluoromethanesulfonyl)imide (MMMP-TFSI) obtained in Example 3. The compounds were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

EXAMPLE 75

Lithium bistetrafluoroborate (LiBF$_4$) was admixed with the N-methoxymethyl-N-methylpyrrolidinium bis(trifluoromethanesulfonyl)imide (MMMP-TFSI) obtained in Example 3 at a concentration of 0.6 M. The compounds were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

EXAMPLE 76

The N-methoxymethyl-N-methylpyrrolidinium bis(trifluoromethanesulfonyl)imide (MMMP-TFSI) obtained in Example 3 was admixed at varying concentrations with a mixture of ethylene carbonate (EC) and ethylmethyl carbonate (EMC) (product of Kishida Chemical Co., Ltd., lithium battery grade, EC:EMC volume ratio=1:3), and lithium bis(trifluoromethanesulfonyl)imide (LiTFSI) was admixed at a concentration of 0.6 M with each of the resulting solutions. The compounds were mixed together within a dry box having a nitrogen atmosphere, up to −60° C. in dew point. The solutions prepared were checked for water content by a Karl Fischer moisture meter (Hiranuma Moisture Meter AQ-7, product of Hiranuma Sangyo Co., Ltd.) and found to be up to 30 ppm in water content. Table 14 shows the compositions of the solutions.

COMPARATIVE EXAMPLE 37

Lithium tetrafluoroborate (LiBF$_4$) was admixed with the N,N-diethyl-N-methoxyethyl-N-methylammonium tetrafluoroborate (DEMME-BF$_4$) obtained in Comparative Example 9 at a concentration of 0.6 M. The tetrafluoroborates were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

COMPARATIVE EXAMPLE 38

Lithium bis(trifluoromethanesulfonyl)imide (LiTFSI) was admixed with the N,N-diethyl-N-methoxyethyl-N-methylammonium bis(trifluoromethanesulfonyl)imide (DEMME-TFSI) obtained in Comparative Example 10 at a concentration of 0.6 M. The imides were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

COMPARATIVE EXAMPLE 39

Lithium bis(trifluoromethanesulfonyl)imide (LiTFSI) and lithium tetrafluoroborate (LiBF$_4$) were admixed at respective concentrations of 0.4 M and 0.2 M with the N,N-diethyl-N-methoxyethyl-N-methylammonium bis(trifluoromethanesulfonyl)imide (DEMME-TFSI) obtained in Comparative Example 10. The compounds were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

COMPARATIVE EXAMPLE 40

Lithium tetrafluoroborate (LiBF$_4$) was admixed with the N,N-diethyl-N-methoxyethyl-N-methylammonium bis(trifluoromethanesulfonyl)imide (DEMME-TFSI) obtained in Comparative Example 10 at a concentration of 0.6 M. The compounds were mixed together within a dry box having a nitrogen atmosphere, up to −60° C. in dew point. The solution prepared was checked for water content by a Karl Fischer moisture meter (Hiranuma Moisture Meter AQ-7, product of Hiranuma Sangyo Co., Ltd.) and found to be up to 30 ppm in water content.

COMPARATIVE EXAMPLE 41

The N,N-diethyl-N-methoxyethyl-N-methylammonium bis(trifluoromethanesulfonyl)imide (DEMME-TFSI) obtained in Example 10 was admixed at varying concentrations with a mixture of ethylene carbonate (EC) and ethylmethyl carbonate (EMC) (product of Kishida Chemical Co., Ltd., lithium battery grade, EC:EMC volume ratio=1:3), and lithium bis(trifluoromethanesulfonyl)imide (LiTFSI) was admixed at a concentration of 0.6 M with each of the resulting solutions. The compounds were mixed together within a dry box having a nitrogen atmosphere, up to −60° C. in dew point. The solutions prepared were checked for water content by a Karl Fischer moisture meter (Hiranuma Moisture Meter AQ-7, product of Hiranuma Sangyo Co., Ltd.) and found to be up to 30 ppm in water content. Table 44 shows the compositions of the solutions.

<Measurement of Electrical Conductivity>

The electrolytic solutions of Examples 72 to 76 and Comparative. Examples 37 to 41 were checked for electrical conductivity. A conductivity meter (CDM210, product of Radiometer Analytical SAS) was used for measuring the electrical conductivity.

The measuring cell used was XE-100 (product of Radiometer Analytical SAS). Tables 44 to 46 show the results.

TABLE 44

| electrolytic solution | composition | electrical conductivity (mScm$^{-1}$) (25° C.) |
|---|---|---|
| Ex. 72 | 0.6M LiBF$_4$/MMMP-BF$_4$ | 4.4 |
| Ex. 73 | 0.6M LiTFSI/MMMP-TFSI | 1.9 |
| Ex. 74 | 0.4M LiTFSI + 0.2M LiBF$_4$/MMMP-TFSI | 2.4 |
| Ex. 75 | 0.6M LiBF$_4$/MMMP-TFSI | 2.4 |
| Com. Ex. 37 | 0.6M LiBF$_4$/DEMME-BF$_4$ | 0.8 |
| Com. Ex. 38 | 0.6M LiTFSI/DEMME-TFSI | 1.0 |
| Com. Ex. 39 | 0.4M LiTFSI + 0.2M LiBF$_4$/DEMME-TFSI | 1.3 |
| Com. Ex. 40 | 0.6M LiBF$_4$/DEMME-TFSI | 1.4 |

TABLE 45

| concentration of lithium salt | solvent composition of electrolytic solution in Ex. 76 (wt %) | | electrical conductivity (mScm$^{-1}$) (25° C.) |
|---|---|---|---|
| | MMMP-TFSI | EC + EMC (volume ratio EC:EMC = 1:3) | |
| 0.6M(LiTFSI) | 0 | 100 | 7.1 |
| | 10 | 90 | 8.8 |
| | 20 | 80 | 9.7 |
| | 30 | 70 | 10.7 |
| | 40 | 60 | 10.0 |

TABLE 46

| concentration of lithium salt | solvent composition of electrolytic solution in Com. Ex. 41 (wt %) | | electrical conductivity (mScm$^{-1}$) (25° C.) |
|---|---|---|---|
| | DEMME-TFSI | EC + EMC (volume ratio EC:EMC = 1:3) | |
| 0.6M(LiTFSI) | 0 | 100 | 7.1 |
| | 10 | 90 | 8.5 |
| | 20 | 80 | 8.8 |
| | 30 | 70 | 9.4 |
| | 40 | 60 | 9.3 |

<Fabrication of Lithium Secondary Cells>

EXAMPLE 77

Figure 9:
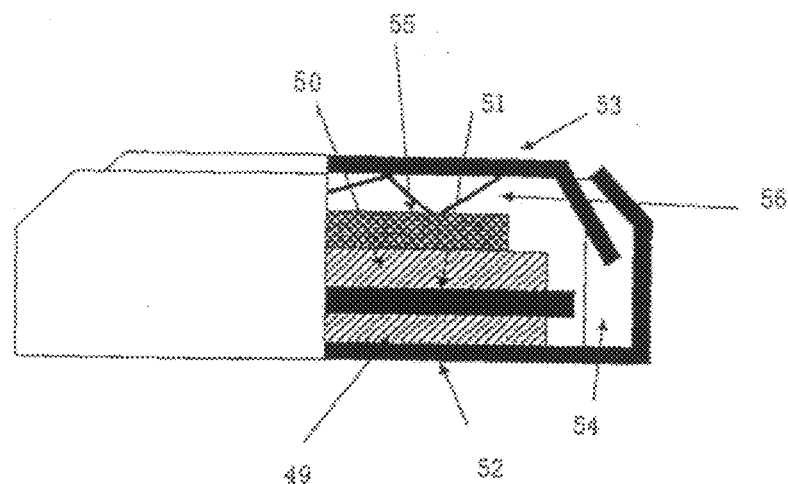
FIG. 9 is a sectional view showing a coin-shaped lithium secondary cell.

FIG. 9 shows a coin-shaped lithium secondary cell. With reference to FIG. 9, indicated at 49 is a positive electrode, at 50 a negative electrode, at 51 a separator, at 52 a positive electrode can, at 53 a negative electrode can, at 54 a gasket, at 55 a spacer, and at 56 a spring. The lithium secondary cell shown in FIG. 9 was fabricated by the following procedure. The positive electrode can 52, negative electrode can 53, spacer 55 and spring 56 used were made of stainless steel. The negative electrode 50 used was made from metal lithium foil having a thickness of 200 μm, by cutting out a circular shape. To make the positive electrode 49, a powder of LiCoO$_2$, acetylene black serving as an auxiliary conductive agent and PVdF serving as a binder were mixed together in the ratio of 85:10:5, and the mixture was made into a paste with addition of N-methylpyrrolidone. Aluminum foil, 30 μm in thickness, was uniformly coated with the paste with an applicator for use in electrode coating. The coated foil was then dried in a vacuum at 120° C. for 8 hours and cut out in a circular shape by an electrode blanking machine to obtain the positive electrode 49. The separator and the blanked-out positive electrode were impregnated with the electrolytic solution obtained in Example 73. The positive electrode was placed on the bottom wall of the positive electrode can 52, the separator was placed on the electrode, and the gasket 54 was placed into the can 52. The negative electrode 50, spacer 55, spring 56 and negative electrode can 53 were placed one after another over the separator, and an opening portion of the positive electrode can 52 was inwardly folded using a cell crimping machine to seal off the opening and fabricate a lithium secondary cell.

Lithium secondary cells were fabricated by the same procedure as in Example 77 with the exception of using the electrolytes listed in Table 47 in Example 78 and Comparative Examples 42, 43.

Figure 10:
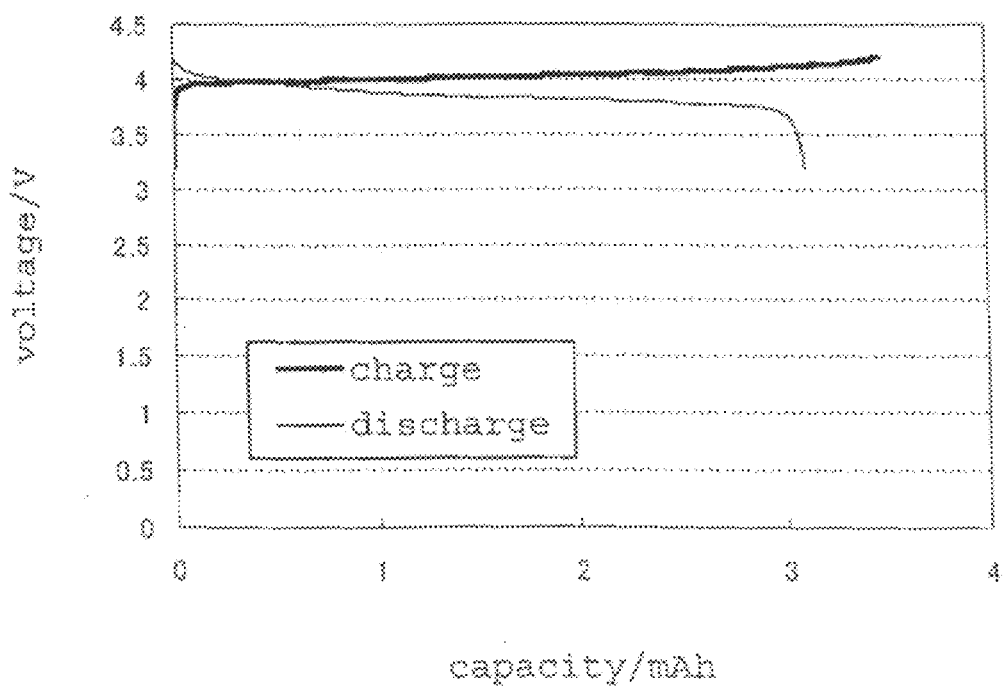
FIG. 10 is a charge-discharge curve of Example 77.

The cells thus fabricated were subjected to a charge-discharge test in the following manner. Each cell was charged with a constant current of 0.21 mA, and upon the voltage reaching 4.2 V, the cell was charged with a constant voltage of 4.2 V for 30 minutes. The cell was discharged to voltage of 3 V at constant current of 0.21 mA. Upon the voltage reaching voltage of 3 V, the cell was held at 3 V for 30 minutes. These charge and discharge steps were combined together as one cycle. FIG. 10 shows the charge-discharge curve obtained in Example 77. For comparison, Table 47 shows iR loss values of Example 78 and Comparative Examples 42, 43 relative to the iR loss value obtained in Example 77 immediately after discharging and taken as 100.

TABLE 47

|  | electrolytic solution | iR drop |
|---|---|---|
| Ex. 77 | Ex. 73 | 100 |
| Ex. 78 | Ex. 74 | 58 |
| Com. Ex. 42 | Com. Ex. 38 | 171 |
| Com. Ex. 43 | Com. Ex. 39 | 135 |

INDUSRIAL APPLICABILITY

The use of electrolytes of the invention provides electrolytic solutions having high voltage resistance and high electrical conductivity. When dissolved in a solvent, the electrolyte of the invention affords an electrolytic solution having a high electrolyte concentration and superior in electrical conductivity to electrolytic solutions obtained by dissolving conventional solid electrolytes in organic solvents. Consequently, the electrolytic solution of the invention provides electrochemical devices useful at a high voltage, having a high discharge capacity and exhibiting great current discharge performance. The electrolyte is also highly soluble in chain carbonates and suited to uses requiring high voltage resistance.

The invention claimed is:

1. A composition consisting of a quaternary ammonium salt of the formula (1)

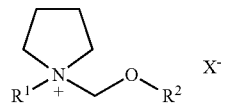

(1)

wherein R1~R2 are both methyl, and X⁻ is $N(CF_3SO_2)_2^-$, and an organic solvent selected from the group consisting of cyclic carbonic acid esters, chain carbonic acid esters, nitrile compounds and sulfone compounds.

2. The composition according to claim 1, wherein the organic solvent consists of one or at least two of said organic solvents selected from among cyclic carbonic acid esters, chain carbonic acid esters, nitrile compounds and sulfone compounds.

3. The composition according to claim 1, wherein the organic solvent comprises one or at least two organic solvents is selected from the group consisting of propylene carbonate, dimethyl carbonate, ethylmethyl carbonate, acetonitrile and sulfolane.

4. The composition according to claim 1, wherein the organic solvent is propylene carbonate.

5. The composition according to claim 1, wherein the organic solvent is dimethyl carbonate.

6. The composition according to claim 1, wherein the organic solvent is ethylmethyl carbonate.

7. The composition according to claim 1, wherein the organic solvent is acetonitrile.

8. The composition according to claim 1, wherein the organic solvent is a mixture of at least two organic solvents selected from among propylene carbonate, ethylene carbonate, dimethyl carbonate and ethylmethyl carbonate.

9. The composition according to claim 1, wherein the organic solvent is an organic solvent mixture comprising dimethyl carbonate and ethylmethyl carbonate.

10. An electrochemical device comprising, as an electrolytic solution, the composition of claim 1.

11. The composition according to claim 1, wherein the organic solvent is selected from the group consisting of cyclic carbonic acid esters, nitrile compounds and sulfone compounds.

12. The composition according to claim 11, wherein the organic solvent is selected from the group consisting of propylene carbonate, ethylmethyl carbonate, acetonitrile and sulfolane.

* * * * *